US006392085B2

(12) United States Patent
Daluge et al.

(10) Patent No.: US 6,392,085 B2
(45) Date of Patent: *May 21, 2002

(54) THERAPEUTIC NUCLEOSIDES

(75) Inventors: Susan Mary Daluge, Chapel Hill, NC (US); Douglas Alan Livingston, San Diego, CA (US)

(73) Assignee: SmithKline Beecham Corporation, Philadelphia, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/113,793

(22) Filed: Jul. 10, 1998

Related U.S. Application Data

(63) Continuation of application No. 08/746,034, filed on Nov. 6, 1996, now abandoned, which is a continuation of application No. 08/295,656, filed as application No. PCT/GB93/00378 on Feb. 24, 1993, now Pat. No. 5,641,889.

(30) Foreign Application Priority Data

Feb. 25, 1992 (GB) .............................. 9204015

(51) Int. Cl.$^7$ ............................................ C07C 271/12
(52) U.S. Cl. ........................................................ 560/115
(58) Field of Search ........................................ 560/115

(56) References Cited

U.S. PATENT DOCUMENTS

| | | | |
|---|---|---|---|
| 4,543,255 A | 9/1985 | Shealy | 210/390 |
| 4,734,194 A | 3/1988 | Kalman et al. | 210/390 |
| 5,087,697 A | 2/1992 | Daluge | 544/323 |
| 5,206,435 A | 4/1993 | Daluge | 564/1 |
| 5,641,889 A | 6/1997 | Daluge | 564/1 |
| 5,808,147 A | 9/1998 | Daluge | 562/504 |

FOREIGN PATENT DOCUMENTS

| | | |
|---|---|---|
| EP | 0 219 838 A2 | 4/1987 |
| EP | 0 236 935 A2 | 9/1987 |
| EP | 0 278 501 A2 | 8/1988 |
| EP | 0 424 064 A1 | 4/1991 |
| EP | 0 434 450 A2 | 6/1991 |
| JP | 60-139653 * | 7/1985 |
| WO | 90/06671 | 6/1990 |
| WO | 91/13549 | 9/1991 |

OTHER PUBLICATIONS

Mekrami et al. Tetrahydron Asynmetry, vol. 3, No. 3, pp. 431–436, 1992.*

Daluge, S.M. et al., An Efficient, Scalable Synthesis of the HIV Reverse Transcriptase Inhibitor Ziagen® (1592U89), in: Nucleoside, Nucleotides & Nucleic Acids, ed. J.A. Secrist, vol. 19 (1&2), 297–327, 2000.

Dickman et al., "Reduction of a–Amino Acids: L–Valinol," *Org. Syn. Coll.* vol. VII, 1990, 530–533.

Price, "Inhibition of the replication of hepatitis B virus by the carbocyclic analogue of 2'–deoxyguanosine," *Proc. Natl. Acad. Sci. USA* vol. 86, Nov., 1989, 8541–8544.

Evans, "Synthesis of Either Enantiometer of cis–3–Aminocyclopentanecarboxylic Acid from Both Enantiomers of Racemic 2–Azabicyclo [2.2.1]hept–5–en–one", *Royal Society of Chemistry. Perkins Transaction* 1, vol. 3, Mar. 1991, 656–657.

Dornsife et. al., "Anti–Human Immunodeficiency Virus Synergism by Zidovudine (3'–Azidothymidine) and Didanosine (Dieoxyinosine) Contrasts with Their Additive Inhibition of Normal Human Marrow Progenitor Cells," *Antimicrob. Agents Chemother.*, 35, 1991, 322–328.

Katagiri et. al., "Synthesis of Nucleosides and Related Compounds. XXII. α Carbocyclic Analogues of Thymidine and Related Compounds from 2–Azibicyclo [2.2.1] hept–5–en–3–ones," *Chem. Pharm. Bull.* 39, 1991, 1682–1688.

Bennett et al., "Phosphorylation of the Carboyclic Analog of 2'Deoxyguanosine in Cells Infected with Herpes Viruses," *Biochemical Pharmacology*, 1990, vol. 40, No. 7, 1515–1522.

Balzarini et al., "Carbocyclic 5–Iodo–2'–deoxyuridine (C–IDU) and Carbocyclic (E)–5–(2–Bromovinyl)–2'–deoxyuridine (C–BVDU) as Unique Examples of Chiral Molecules where the Two Enantiomeric Forms Are Biologically Active: Interaction of the (+) and (–)–Enantiomers of C–IDU and C–BVDU with the Thymidine Kinase of Herpes Simplex Virus Type 1", *Molec. Pharm.* 37,. 1990, 395–401.

Bruckner et al., "Automated Enantioseparation of Amino Acids By Derivitization with 0–Phthaldialdehyde and N–Acylated Cysteines," *J. Chrom.*, 476, 1989, 73–82.

Biggadike et al., "Short Convergent Route to Homochiral Carbocyclic 2'–Deoxynucleosides and Carbocyclic Ribonucleosides," *J. Chem. Soc. Chem Commun.*, 1987, 1083–1084.

Barton et al., "On the Mechanism of the Deoxygenation of Secondary Alcohols by the Reduction of Their Methyl Xanthates By Tin Hydrides," *Tetrahedron*, 42, 1986, 2329–2338.

Powell et al., "Lithium Aluminum Hydride Reductions: a New Hydrolysis Method for Intractable Products," *Synthesis*, 1986, 338–340.

Robins et al, Nucleic Acid Related Compounds 42. A General Procedure for the Efficient Deoxygenation of Secondary Alcohols. Regiospecific and Steroselective conversion of Ribonucleosides to 2'–Deoxynucleosides, *J. Am. Chem. Soc.*, 105, 1983, 4059–4065.

Hartwig, "Modern Methods for the Radical Deoxygenation of Alcohols," *Tetrahedron*, 1983, 39, 2609–2645.

(List continued on next page.)

Primary Examiner—Shailendra Kumar
(74) Attorney, Agent, or Firm—Amy H. Fix

(57) ABSTRACT

The present invention relates to intermediates useful for the preparation of certain compounds, for example, purine carbocyclic nucleosides.

3 Claims, No Drawings

OTHER PUBLICATIONS

Barton, et al., "Radical–Induces Deoxygenation of Primary Alcohols," *Synthesis*, 1981, 743–745.

Oberg et al., "The Tetraisopropyldisiloxane–1,3–Diyl: A Versatile Protecting Group for the Synthesis of Adenylyl–2(2'→5')–Adenyly–(2'→5')–Adenosine (2–5A Core)," *Tetrahedron Letters* 22, 1981, 1741–1744.

Robins et al., Smooth and Efficient Deoxygenation of Secondary Alcohols. A General Procedure for the Conversion of Ribonucleosides to 2' Deoxynucleosides,*J. Am. Chem. Soc.*, 103, 1981, 932–933.

Verdegaal et al., "A Convient Synthesis of 2' O–acetal–N–acyl derivatives of riboguanosine," *Recueil*, 10, 1981, 200–204.

Markiewicz, "The Reaction of 1,3–Dichloro–1,1,3,3–Tetrisopropyldisoloxane With Some Chain Polyhydroxy Compounds," *Tetrahedron Letters*, 21, 1980, 4523–4524.

Markiewicz, "Tetraisoproipyldisiloxane–1,3–diyl, a Group for Simultaneous Protection of 3'–and 5'–Hydroxy Functions of Nucleosides," *J.Chem.Research* (S) 1979, 24–25.

Barton et al., "A new Method for the Deoxygenation of Secondary Alcohols," *J.Chem.Soc., Perkin*, 1975, 1574–1585.

Jagt et al., "Diels–Alder Cycloadditions of Sulfonyl Cyandines with Cyclopentadienne. Synthesis of 2–Azabicyclo [2.2.1]hepta–2,5–dienes," *J.Org. Chem.*, 39, 1974, 564–566.

Yamamoto and Maruoka, "Regioselective Carbonyl Amination using Diisobutylaluminum Hydride", *J.Am.Chem.Soc,* 14, 1981, 4186–4194.

Markiewicz et al., "The Reaction of 1,3–Dichloro–1,1,3, 3–Tetraisopropyldisiloxane with Cytosine Arabinoside and 1–(6–Deoxy–α–L–Talofuranosyl)Uracil", *Collection Czechoslov. Chem Commun.*, (English) vol. 45(6), 1980, 1860–1865.

Secrist III et al., "Resolution of Racemic Carbocyclic Analogues of Purine Nucleosides through the Action of Adenosine Deaminase, Antiviral Activity of the Carbocyclc 2'–Deoxyguanosine Enantiomers",*J. Med. Chem.*, (30), 1987, 746–749.

Shealy et al., "Synthesis and Antiviral Activity of Carboyclcic Analogues of 2'–Deoxyribofuranosides of 2–Amino–6–substituted Purines and of 2–amino–6–substituted–8–azapurines," *J. Med.Chem.*, 27, 1984, 1416–1421.

Schroder, "Osmium Tetroxide Cis Hydroylation of Unsaturated Substrates," *Chem Rev.* 1980 (80), 187–213.

VanRheenen et al., "An Improved Catalytic $OsO_4$ oxidation of Olefins to Cis–1–2–Glycols Using Tertiary Amine Oxides as the Oxidant," *Tetrahedron Letters*, No. 3, 1976, 1973–1976.

Tyle, "Iontophoretic Devices for Drug Delivery," *Pharmaceutical Research* (3), 1986, 318–326.

Allan et al, "Synthesis of Analogues of GABA. IV Three Unsaturated Derivatives of 3–Aminocyclopentane–1–carboxylic acid," *Aust. J. Chem.*, 33, 1980, 599–604.

* cited by examiner

THERAPEUTIC NUCLEOSIDES

This is a continuation of application Ser. No. 08/746,034, filed Nov. 6, 1996, now abandoned, which is a continuation of Ser. No. 08/295,656, filed Sep. 12, 1994, now U.S. Pat. No. 5,641,889, which is a §371 of PCT/GB93/00378, filed Feb. 24, 1993, which claims priority from GB 9204015, filed Feb. 25, 1992.

The present invention relates to purine nucleoside analogues containing a carbocyclic ring in place of the sugar residue, pharmaceutically acceptable derivatives thereof, and their use in medical therapy, particularly for the treatment of certain viral infections.

Hepatitis B virus (HBV) is a small DNA containing virus which infects humans. It is a member of the class of closely related viruses known as the hepadnaviruses, each member of which selectively infects either mammalian or avian hosts, such as the woodchuck and the duck.

Worldwide, HBV is a viral pathogen of major consequence. It is most common in Asian countries, and prevalent in sub-Saharan Africa. The virus is etiologically associated with primary hepatocellular carcinoma and is thought to cause 80% of the world's liver cancer. In the United States more than ten thousand people are hospitalized for HBV illness each year, an average of 250 die with fulminant disease.

The United States currently contains an estimated pool of 500,000-1 million infectious carriers. Chronic active hepatitis will develop in over 25% of carriers, and often progresses to cirrhosis. It is estimated that 5000 people die from HBV-related cirrhosis each year in the USA, and that perhaps 1000 die from HBV-related liver cancer. Even when a universal HBV vaccine is in place, the need for effective anti-HBV compounds will continue. The large reservoir of persistently infected carriers, estimated at 220 million worldwide, will receive no benefit from vaccination and will continue at high risk for HBV-induced liver disease. This carrier population serves as the source of infection of susceptible individuals perpetuating the instance of disease particularly in endemic areas or high risk groups such as IV drug abusers and homosexuals. Thus, there is a great need for effective antiviral agents, both to control the chronic infection and reduce progression to hepatocellular carcinoma.

Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease as outlined above. In "Viral Infections of Humans" (second edition, Ed., Evans, A. S. (1982) Plenum Publishing Corporation, New York), Chapter 12 describes in detail the etiology of viral hepatitis infections.

Of the DNA viruses, the herpes group is the source of many common viral illnesses in man. The group includes cytomegalovirus (CMV), Epstein-Barr virus (EBV), varicella zoster virus (VZV), herpes simplex virus (HSV) and human herpes virus 6 (HHV6).

In common with other herpes viruses, infection with CMV leads to a life-long association of virus and host and, following a primary infection, virus may be shed for a number of years. Clinical effects range from death and gross disease (microcephaly, hepatosplenemegaly, jaundice, mental retardation) through failure to thrive, susceptibility to chest and ear infections to a lack of any obvious ill effect. CMV infection in AIDS patients is a predominant cause of morbidity as, in 40 to 80% of the adult population, it is present in a latent form and can be reactivated in immunocompromised patients.

EBV causes infectious mononucleosis and isalso suggested as the causative agent of nasopharyngeal cancer, immunoblastic lymphoma, Burkitt's lymphoma and hairy leukoplakia.

VZV causes chicken pox and shingles. Chicken pox is the primary disease produced in a host without immunity. In young children, it is usually a mild illness characterized by a vesicular rash and fever. Shingles is the recurrent form of the disease which occurs in adults who were previously infected with varicella. The clinical manifestations of shingles include neuralgia and a vesicular skin rash that is unilateral and dermatomal in distribution. Spread of inflammation may lead to paralysis or convulsionsand coma can occur if the meninges becomes affected. In immunodeficient patients, VZV may disseminate causing serious or even fatal illness.

HSV 1 and HSV 2 are some of the most common infectious agents of man. Most of these viruses are able to persist in the host's neural cells. Once infected, individuals are at risk of recurrent clinical manifestation of infection which can be both physically and psychologically distressing. HSV infection is often characterized by extensive lesions of the skin, mouth and/or genitals. Primary infections may be subclinical although they tend to be more severe than infections in individuals previously exposed to the virus. Ocular infections by HSV can lead to keratitis or cataracts. Infection in the newborn, in immunocompromised patients or penetration of infection into the central nervous system can prove fatal. HHV6 is the causative agent of roseola infantum (exanthum subitum) in children which is characterized by fever and the appearance of a rash after the fever has dedined. HHV6 has also been implicated in syndromes of fever and/or rash and pneumonia or hapatitis in immunocompromised patients.

It has been reported thatthe carbocyclic anaiogue of 2'-deoxyguanosine (2'-CDG) i.e. (1R*, 3S*, 4R)-2-amino-1,9-dihydro-9-[3-hydroxy-4-hydroxymethyl)cyclopentyl]-6H-purine-6-one, is active against several viruses. Thus in Proc. Natl. Acad. Sci. USA 1989, Vol. 86, pp 8541-8544, it is disclosed that 2'-CDG inhibits hepatitis B viral replication. 1. Med. Chem (1987) 30, pp 746-749 and Biochemical Pharmacology (1990) Vol. 40, No. 7, pp 1515-1522, report 2'-CDG, especially the (+)-enantiomer, as active against herpes simplex virus type 1 (HSV-1). Furthermore 2'-CDG and general analogues thereof are disclosed together with a plurality of other compounds in the following patent publications: U.S. Pat. No. 4,543,255 (with reference to HSV 1 and 2), PCT 90/06671 (with reference to hepatitis B), EP 219838, PCT 91/13549 (with reference to cytomegalovirus (CMV)). Other publication relating to 2'-CDG and the preparation thereof are J. Med. Chem. (1984) 27, pp 1416-1421, and J. Chem. Soc. Chem. Commun. (1987) pp 1083-1084.

It has now been discovered that certain analogues of 2'-CDG as referred to below, are useful for the treatment or prophylaxis of certain viral infections. According to a first aspect of the present invention, novel compounds of the formula (I) are provided:

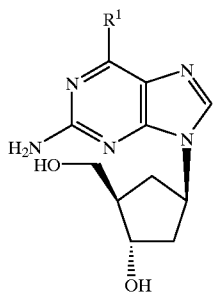

(I)

wherein R¹ represents
hydrogen;
$C_{3-8}$ alkenyloxy; $C_{3-8}$ cycloalkoxy (e.g. cyclopentoxy); $C_{4-8}$ cycloalkenyloxy (e.g. cyclopenten-3-yloxy); aryloxy (e.g. phenoxy) or arylalkoxy (e.g. benzyloxy) in which the aryl may be substituted with one or more $C_{1-4}$ alkyl, halogen, hydroxy, $C_{1-4}$ alkoxy, amino or nitro;
$C_{3-6}$ alkenylthio (e.g. allylthio); $C_{3-6}$ cycloalkylthio; $C_{4-8}$ cycloalkenylthio; arylthio (e.g. phenyithio) or arylalkylthio (e.g. benzylthio) in which the aryl may be substituted with one or more $C_{1-4}$ alkyl, halogen, hydroxy, $C_{1-4}$ alkoxy, amino or nitro;
an amino group, —NR²R³, in wnich R² and R³ may be the same or different and are independently selected from hydrogen; $C_{1-8}$ alkyl; $C_{1-6}$ alkoxy; $C_{1-6}$ hydroxyalkyl (e.g. hydroxyethyl); $C_{1-6}$ alkoxyalkyl (e.g. methoxyethyl); $C_{3-7}$ cycloalkyl (e.g. cyclopropyl, cyclobutyl or cyctopentyl) in which the cycloalkyl may be substituted by one or more $C_{1-6}$ alkyl or hydroxy; aryl (e.g. phenyl) or aralkyl (e.g. benzyl) in which the aryl may be substituted with one or more $C_{1-4}$ alkyl, halogen, hydroxy, $C_{1-4}$ alkoxy, amino or nitro; $C_{3-6}$ alkenyl (e.g. allyl); or R² and R³ together form a 4- to 8-membered ring (e.g. azetidinyl or pyrrolidinyl); provided that R² and R³ cannot both be hydrogen or both be $C_{1-8}$ alkyl;
4-morpholinyl, 1-piperazinyl or 1-pyrrallyl;
or a pharmaceutically acceptable derivative thereof.

It is to be understood that the present invention encompasses the particular enantiomers depicted in formula (I), including tautomers of the purine, alone and in combination with their mirror-image enantiomers which are not depicted. Enantiomers depicted by formula (I), the "relevant" enantiomers, are preferred and more preferably the relevant enantiomer is provided substantially free of the corresponding enantiomer to the extent that it is generally in admixture with less than 10% w/w, preferably less than 5% w/w, more preferably less than 2% w/w and most preferably less than 1% w/w of the corresponding enantiomer based on the total weight of the mixture.

However, the processes disclosed pertain to the preparation opposite enantiomers via Examples 11-17 and Example 34.

Where reference herein is madeto an alkyl moiety, this includes methyl, ethyl, n-propyl, isopropyl, n-butyl, iso-butyl, tert-butyl, n-pentyl, iso-pentyl, neopentyl and hexyl.

Furthermore reference to $C_{3-7}$ cycloalkyl includes cyclopropyl, cyclobutyl, cyclopentyl, cyclohexyl and cycloheptyl.

Preferably R¹ represents a $C_{3-7}$ cycloalkylamino most preferably cyclopropyl.

Particularly preferred examples of compounds of formula (I), exhibiting decreased toxicity compared to 2'-CDG, are:
a) (+)-(1S, 2R, 4R)-4-(2-amino-6-(cyclopropylamino)-9H-purin-9-yl)-2-(hydroxymethyl)-1-cyclopentanol b) (+)-(1S, 2R, 4S)-4-(2-amino-6-(cyclopropyimethylamino)-9H-purin-9yl)-2-(hydroxymethyl)-1-cyclopentanol
c) (+)-(1S, 2R, 4R)-4-(2-amino-6-(1-pyrrolidinyl)-9H-purin-9-yl)-2-(hydroxymethyl)-1-cyclopentanol
d) (+)-(1S, 2R, 4R)-4-[6-(allylthio)-2-amino-9H-purin-9-yl]-2-(hydroxymethylg)-1-cyclopentanol
e) (+)-(1S, 2R, 4R)-4-(2-amino-6-(cyclopentyloxy)-9H-purin-9-yl)-2-(hydroxymethyl)-1-cyclopentanol
f) (+)-(1S, 2R, 4R)-4-(2-amino-(1-azietidinyl)-9H-purin-9yl)-2-(hydroxymethyi)-1-cyclopentanol
and pharmaceutically acceptable salts thereof.

The compounds of formula (I) above and their pharmaceutically acceptable derivatives are herein referred to asthe compounds according to the invention.

In a further aspect of the invention there are provided the compounds according to the invention for use in medical therapy particularly for the treatment or prophylaxis of viral infections such as hepadnaviral infections and herpes viral infections. To date compounds of the invention has been shown to be active against hepatitis B virus (HBV) and cytomegalovirus (CMV) infections, although early results also suggest that the invention could also be active against other herpes virus infections such as EBV, VZV, HSVI and II and HHHV6.

Other viral conditions which may be treated in accordance with the invention have been discussed in the introduction hereinbefore.

In yet a further aspect of the present invention there is provided:
a) A method for the treatment or prophylaxis of a hepadnaviral infection such as hepatitis B or a herpes viral infection such as CMV which comprises treating the subject with a therapeutically effective amount of a compound according to the invention.
b) Use of a compound according to the invention in the manufacture of a medicament for the treatment or propnylaxis of any of the above-mentioned infections or conditions.

By "a pharmaceutically acceptable derivative" is meant any pharmaceutically or pharmacologically acceptable salt, ester or salt of such ester of a compound according to the invention, or any compound which, upon administration to the recipient, is capable of providing (directly or indirectly) a compound according to the invention, or an antivirally active metabolite or residue thereof.

Preferred esters of the compounds of the invention include carboxyiic acid esters in which the non-carbonyl moiety of the ester grouping is selected from straight or branched chain alkyl, e.g. n-propyl, t-butyl, n-butyl, alkoxy-alkyl (e.g. methoxymethyl), aralkyl (e.g. benzyl), aryloxy-alkyl (e.g. phenoxymethyl), aryl (e.g. phenyl optionally substituted by halogen, $C_{1-4}$ alkyl or $C_{1-4}$ alkoxy or amino); sulfonate esters such as alkyl- or aralkylsulfonyl (e.g. methanesulfonyl); amino acid esters (e.g. L-valyl or L-isoleucyl); and mono-, di- or triphosphate esters. The phosphate esters may be further esterified by, for example, a $C_{1-20}$ alcohol or reactive derivativethereof, or by a 2,3-di ($C_{2-24}$)acyl glycerol.

With regard to the above-descrbed esters, unless otherwise specified, any alkyl moiety presentadvantageously contains 1 to 18 carbon atoms, particularly 3 to 6 carbon atoms such as the pentanoate. Any aryl moiety present in such esters advantageously comprises a phenyl group.

Any reference to any of the above compounds also includes a reference to a pharmaceutically acceptable salt thereof.

Pharmaceutically acceptable salts include salts of organic carboxylic acids such as acetic, lactic, tartaric, malic, isethionic, lactobionic, p-aminobenzoic and succinic adds; organic sulfonic acids such as methanesulfonic, ethanesulfonic, benzenesulfonic and p-toluenesulfonic acids and inorganic adds such as hydrochloric, sulfuric, phosphoric and sulfamic acids.

The above compounds according to the invention and their pharmaceutically acceptable derivatives may be employed in combination with other therapeutic agents for the treatment of the above infections or conditions. Examples of such further therapeutic agents include agents that are effective for the treatment of viral infections or associated conditions such as acyclic nucleosides (e.g. acyclovir), immunomodulatory agents such as thymosin, ribonucleotide reductase innibitors such as 2-acetylpyridine 5-[(2-chloroanilino)thiocarbonyl)]thiocarbonohydrazone, interferons such as α-interferon. 1-β-D-arabinofuranosyl-5-(1-propynyl)uracil, 3'-azido-3'-deoxythymidine, ribavirin and phosphonotormic acid. The component compounds of such combination therapy may be administered simultaneously, in either separate or combined formulations, or at different times, e.g. sequentially such that a combined effect is achieved.

The compounds according to the invention, also referred to herein as the active ingredient, may be administered for therapy by any suitable route including oral, rectal, nasal, topical (including transdermal, buccal and sublingual), vaginal and parenteral (including subcutaneous, intramuscular, intravenous and intradermal). It will be appreciated that the preferred route will vary with the condition and age of the recipient, the nature of the infection and the chosen active ingredient.

In general a suitable dose for each of the abovementioned conditions will be in the range of 0.01 to 250 mg per kilogram body weight of the recipient (e.g. a human) per day, preferably in the range of 0.1 to 100 mg per kilogram body weight per day and most preferably in the range 1.0 to 20 mg per kilogram body weight per day. (Unless otherwise indicated, all weights of active ingredient are calculated as the parent compound of formula (I); for salts or esters thereof, the weights would be increased proportionally.) The desired dose is preferably presented as two, three, four, five, six or more sub-doses administered at appropriate intervals throughout the day. These sub-doses may be administered in unit dosage forms, for example, containing 10 to 1000 mg, preferably 20 to 500 mg, and most preferably 100 to 400 mg of active ingredient per unit dosage form.

Ideally, the active ingredient should be administered to achieve peak plasma concentrations of the active compound of from about 0.025 to about 100 $\mu$M, preferably about 0.1 to 70 $\mu$M, most preferably about 0.25 to 50 $\mu$M. This may be achieved, for example, by the intravenous injection of a 0.1 to 5% solution of the active ingredient, optionally in saline, or orally administered as a bolus containing about 0.1 to about 250 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible for the active ingredient to be administered alone it is preferable to present it as a pharmaceutical formulation. The formulations of the present invention comprise at least one active ingredient, as defined above, together with one or more accentable carriers thereof and optionally other therapeutic agents. Each carrier must be "acceptable" in the sense of being compatible with the other ingredients of the formulation and not injurious to the patient. Formulations include those suitable for oral, rectal, nasal, topical (including transdermal buccal and sublingual), vaginal or parenteral (including subcutaneous, intramuscular, intravenous and intradermal) administration. The formulations may conveniently be presented in unit dosage form and may be prepared by any methods well known in the art of pharmacy. Such methods include thestep of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 25%, preferably about 3% to 15%. As one particular possibility, the active compound may be delivered from the patch by electrotransport or iontophoresis as generally described in *Pharmaceutical Research*, 3 (6), 318 (1986).

Formulations of the present invention suitable for oral administration may be presented as discrete units such as capsules, cachets or tablets each containing a predetermined amount of the active ingredient; as a powder or granules, as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropyimethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyimethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia ortragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multidose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agents The present invention further incudes the following process for the preparation of compounds of formuia (I) above and derivatives thereof either alone or in combination with their corresponding enantiomers. The process according to the present invention comprises treating a compound of formula (Ia) either alone or in combination with its enantiomer (wherein Z represents a precursor group forthe said $R^1$ group, $R^1$ defined as in formula (I))

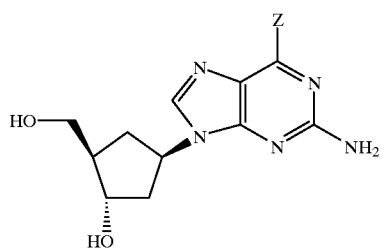

(Ia)

The conversion of (Ia) to (I) may be carried out in a conventional manner, for example, by treatment of a compound of formula (Ia) in which Z represents a leaving group (e.g. a halo such as a chloro group) with an appropriate amine (e.g. methylamine or dimethylamine) or an appropriate alkoxide (e.g. sodium methoxide or potassium n-butoxide) or an appropriate alkylsulfide (e.g. sodium methylmercaptide) or with sodium hydrogen sulfide orthi-curea to provide the 6-thiopurine ($R^1$=mercapto) which is then alkylated with appropriate alkylating agents (e.g. n-propyl iodide, allyl chloride, and dimethyl sulfate) in the presence of an equivalent of base (e.g. sodium hydroxide or potassium t-butoxide) to provide the corresponding alkylthio compoundsof formula (I).

The compounds of formula (Ia) employed as starting materials in the above process may be prepared by reacting a compound of formula (II) either alone or in combination with its enantiomer (wherein Z is defined as in formula (Ia) and $R^4$ and $R^5$ are either the same or differentand may be either hydrogen, formyl, or an amino protecting group such as a $C_{2-6}$ alkanoyl, e.g. acetyl or isobutyryl, or $C_{1-6}$ alkoxycarbonyl, e.g. tert-butoxycarbonyl) with a reactive derivative of formic acid (e.g. triethylorthoformate or diethoxymethyl acetate) optionally with a cosolvent such as dimethyiacetamide or dimethylformamide.

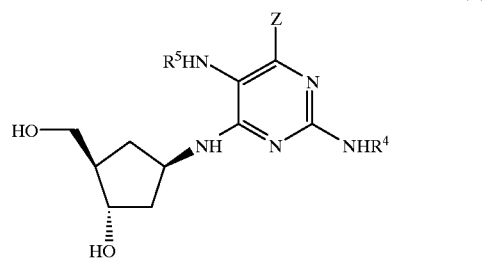

(II)

It is understood that when $R^5$ is other than hydrogen or formyl, deprotection preferably by prior treatment with dilute aqueous mineral acid is required priorto treatment with a reactive derivative of formic acid. In these cases the resulting mineral acid salt of (II) with $R^4$ and $R^5$ being hydrogen is efficiently converted directly to compounds of formula (Ia) by treatment with derivatives of formic acid. e.g. triethylorthoformate, preferably at 25° C. for several hours. When other compounds of formula (II) are reacted with derivatives of formic acid, the reaction is conveniently effected by the addition of slightly more than one equivalent of a strong anhydrous acid, e.g. with 1.1 equivalents of ethanesulfonic acid per equivalent of (II) or 4 equivalents of concentrated aqueous hydrochloric acid per equivalent of (II), preferably at 25° C. It is understood that subsequent treatment of the resulting products with dilute aqueous acid, e.g. 1N hydrochloric acid at 25° C. for several hours cleaves derivatives formed, for example, by reaction of the hydroxy groups with triethyorthoformate.

The compounds of formula (II) employed as starting materials in the above process may be prepared by reacting a compound of formula (IIIa) either alone or in combination with its enantiomer with an appropriately substituted pyrimidine, e.g. 2,5-diamino-4,6-dichloropyrimidine or preferably derivatives thereof, e.g., N-(4,6-dichlor-5-formamido-2-pyrimidinyl) isobutyramide as described in EP 434450, Jun. 26, 1991. This reaction is preferably carried out at 80-120° C., e.g. at reflux in n-butanol or t-butanol with 1-2 equivalents of a base, e.g. triethylamine or potassium carbonate. for 1 to 3 hours.

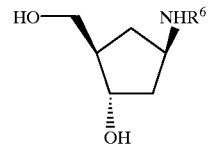

(IIIa) $R^6$ = H
(IIIb) $R^6$ = a protecting group as defined below

The compounds of formula (IIIa), either alone or in combination with their enantiomers, employed as starting materials as described above may be prepared for example by deprotection of protected compounds of formula (IIIb) by methods known in the art (T. W. Greene, "Protective Groups in Organic Synthesis," Wiley, New York, 1981, pp 218-287; J. F. W. McOmie, "Protective Groups in Organic Chemistry," Plenum Press, New York, 1973, pp 43-93)

Most preferably, when $R^6$=tert-butoxycarbonyi (BOC), deprotection can be achieved by the reaction with an acid of pKa less than three as is known in the art and is exemplified below. The amino diol of structure (IIIa) is so obtained in the form of its salt, which is suitable for use in the reaction to prepare compounds of formula (I). The free base of the amino diol (IIIa) is obtained, for example, by contacting the salt with a quaternary ammonium-type anion exchange resin in its hydroxide form as is exemplified below.

The compounds of formula (IIIb) empioyed as starting materials as described above may be prepared for example by desilylation of protected compounds of formula (IVa) by reaction with fluoride ion, as is known in the art and exemplified below (T. W. Greene, "Protective Groups in Organic Synthesis," Wiley, New York, 1981, pp 218-287; J. F. W. McOmie, "Protective Groups in Organic Chemistry," Plenum Press, New York, 1973, pp. 43-93; W. T. Markiewicz, *Tetrahedron Letters* 1980, 21 4523-4524); W. T. Markiewicz and M. Wiewiorowski, *Nucleic Acids Research Special Publication No.* 4, 3185-3188; W. T. Markiewicz, *Chem. Research* (S) 1979, 24-25; C. H. M. Verdegaal, P. L. Jansse, J. F. M. deRooij, G. Veeneman and J. H. vanBoom, *Recueil* 1981, 100, 200-204; C. Gioeli, M. Kwiatkowski, B. Oberg and J. B. Chattopadhyaya, *Tetrahedron Letters* 1981, 22, 1741-1744).

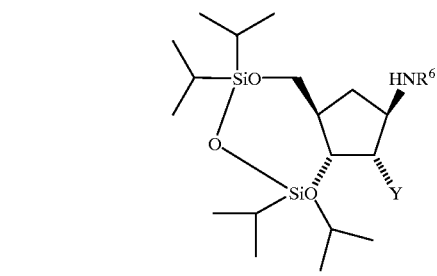

(IVa) Y = H
(IVb) Y = OCSOPh
(IVc) Y = OH $R^6$ = a protecting group as defined below It is surprising in view of the prior art that substantially less than two equivalents of fluoride ion is sufficient to effect deprotecton. in the presentcase approximately one equivalent of tetraethylammonium fluoride was found to be sufficient.

The compounds of formula (IVa) employed as starting materials as described above may be prepared for example by first thiocarbonation of the compounds of formula (IVc) to prepare thiocarbonates of formula (IVb), then reduction of the thiocarbonates of formula (IVb) with e.g. tributyltin hydride as is known in the art (M. J. Robins and J. S. Wilson, *J. Am. Chem. Soc.* 1981, 103, 932-933; M. J. Robins, J. S. Wilson and F. Hansske, *J. Am. Chem. Soc.* 1985, 105, 4059-4065; W. Hartwig, *Tetrahedron* 1993, 39, 2609-2645 and references therein, D. H. R. Barton, D. Crich, A. Lobberding and S. Z. Zard, *Tetrahedron* 1986, 42, 2329-2338; D. H. R. Barton and S. W. McCombie, *J. Chem. Soc., Perkin I* 1975, 1574-1585; D. H. R. Barton, W. B. Motherwell and A. Stange, *Synthesis* 1981, 743-745; N. Katagiri, M. Nomura, M. Muto and C. Kaneko, *Chem. Pharm. Bull.* 1991, 39, 1682-1688) and is exemplified below.

The compounds of formula (IVc) employed as starting materials as descri bed above may be prepared for example by selective protection through reaction of compounds of formula (V) with 1,3-dichloro-1,1,3,3-tetraisopropyl disiloxane as is known in the art (W. T. Markiewicz, N. S. Padyukova, Z. Samek, J. Smrt, *Collection Czechosiov. Chem. Commun.* 1980, 45, 1860-1865; W. T. Markiewicz, *Tetrahedron Letters* 1980, 21, 4523-4524; W. T. Markiewicz and M. Wiewiorowski, *Nucleic Acids Research Special Publication No.* 4, 3185-3188; W. T. Markiewicz, *J. Chem. Research* (S) 1979, 24-25; C. H. M. Verdegaal, P. L. Jansse, J. F. M. deRooij, G. Veeneman and J. H. vanBoom, *Recueil* 1981, 100, 200-204; C. Gioeli, M. Kwiatkowski, B. Oberg and J. B. Chattopadhyaya, *Tetrahedron Letters* 1981, 22, 1741-1744) and is exemplified below.

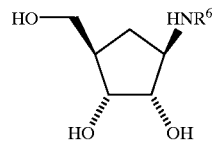

(V)

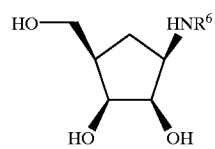

(VI)

$R^6$ = a protecting group as defined below

The compounds of formula (V) employed as starting materials asdescribed above may be prepared for example by cis-dihydroxylation of compounds of structure (VIIa) using a catalytic amount of osmium tetroxide and N-methyl morphotine-N-oxide as is known in the art (V. VanRheenen, R. C Kelly and D. Y. Cha, *Tetrahedron Letters* 1976, 1973-1976; M. Schroder, *Chem. Rev.* 1980, 80, 187-213). The cis-hydroxylation reaction results in a mixture of two geometrical isomers of structure (VI) and (V). The separation of these isomers can be achieved by conventional methods such as chromatography or selective crystallization. The isomers wherein $R^6$ is BOC are most easily separated by crystallization, as is exemplified below.

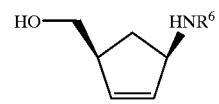

(VIIa) $R^6$ = a protecting group as defined below
(VIIb) $R^6$ = H

The compounds of formula (VIIIa) employed as starting materials as described above maybe prepared for example by protection of the compound of formula (VIIb) by methods known in the art (T. W. Greene, "Protective Groups in Organic Synthesis," Wiley, New York, 1981, pp. 218-287; J. F. W. McOmie, "Protective Groups in Organic Chemistry," Plenam Press, New York, 1973, pp 43-93). Preferred are $R^6$=$C_{2-6}$ alkanoyl (e.g. acetyl) and $C_{2-6}$ alkyloxycarbonyl (e.g. tert-butoxy carbonyl, BOC). Most preferred is R6=BOC, which is exemplified below.

The resolved (–)-amino alcohol of formula (VIIb) or a protected derivative (VIIa) can now be used to synthesize resolved carbocyclic nucleosides, (e.g. (1S, 4R)-4-(2-amino-6-(cyclopropylamino)-9H-purin-9-yl)-2-cyclopentene-1-methanol) as illustrated in EP 434450 (U.S. Pat. No. 5,087, 697) and in the examples hereinafter. Thus, an enantiomer of carbocyclic nucleoside is obtainable by applying reactions that form the corresponding pyrimidine or purine base of the desired nucdeoside, as in known in the art and illustrated herein.

It will be appreciated that the stepsfrom formation of the resolved (–)-amino alcohol of formula (VIIb) up to formation of (1S, 4R)-4-(2-amino-6-(cyclopropylamino)-9H-purin-9-yl)-2-cyclopentene-1-methanol as described in EP 434450 (U.S. Pat. No. 087,697) are incorporated herein by reference, in particular Examples 1-5, 15-19, 26-28 and described herein (Examples 30-33).

Another aspect of the present invention includes a process for the preparation of (–)-(1S, 4R)-4-amino-2-cyclopentene-1-methanol, compound (VIIb), its mirror image enantiomer and mixtures of such enantiomers. Each mirror image enantiomer can be used to prepare in conventional manner antiviral carbocyclic nucleosides of the corresponding enantiomeric configuration, for example as described in Molec Pharm. 37, 395-401 (1990) and J. Med. Chem. 30, 746-749 (1987). This process comprises reducing (–)-(2S, 4R)-4-amino2-cyclopentene-1-carboxylic acid, compound (VIII), the mirror image enantiomer thereof or a mixture of such enantiomers.

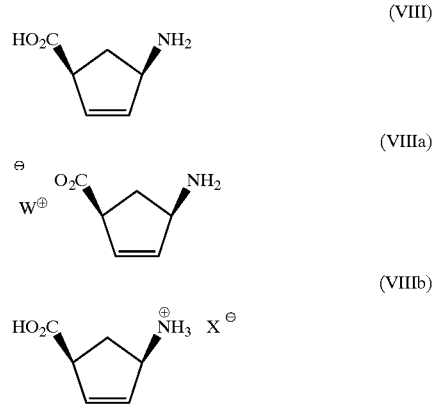

It is preferred that compound (VIII) or its mirror image enantiomer be in the form of a salt, (VIIIa) or (VIIIb). Subsequent references to (VIII), (VIIIa) and (VIIIb) also include the mirror image enantiomers thereof and mixtures of the corresponding enantiomers. Suitable salts (VIIIa) include the lithium, sodium, potassium, magnesium or calcium salts. Most preferred is the sodium salt (W=Na in structure (VIIIa)). Suitable salts (VIIIb) are those wherein the conjugate acid (XH) of the salt posses a pKa less than two. Suitable salts (VIIIb) thus include the hydrochloride, sulphate, bisulphate, hydrobromide, or organic sulphonic acid salt.

It is further preferred that the salt (VIIIb) be an organic sulphonic acid salt. it is most preferred that the organic sulphonic acid salt is a $C_{1-6}$ alkyl sulphonic acid salt (e.g. methanesulphonyl) or aryl sulphonic acid salt (e.g. toluenesulphonyl). In structure (VIIIb), X would thus represent most preferably e.g. a methanesulphonate or toluenesulphonate group, respectively.

The present invention also includes the novel compounds of formulas (VIIIa) and (VIIIb) generically and specifically referred to above.

The reducing agent for conversion of (VIII), (VIIIa), or (VIIIb) to (VIIb) or for conversion of the respective mirror image enantiomers is preferably an aluminum hydride, such as diisobutyl aluminum hydride, sodium bis (2-methoxyethoxy)aluminum hydride, lithium aluminum hydride, sodium aluminum hydride, lithium tri-tert-butoxyaluminohydride, etc. Most preferred is lithium aluminum hydride (D. A. Dickman, A. I. Meyers, G. A. Smith and R. E. Cawley, Org. Syn. Coll. Vol VII, 530-533). Advantageously a source of fluoride ion such as NaF (H. Yamamoto and K. Maruoka, *J. Org Chem.* 1981, 103 4186-4194) isalso used to help release the product from contaminating aluminum following the reduction reaction. Triethanolamine (J. Powell, N. James and S. J Smith, *Synthesis,* 1986, 338-340) can be used in place of fluoride, but is less preferred.

The solvent for the reduction reaction is preferably an ether such as THF. It is further preferred that water (1-15% w/w) be added to the ether prior to isolation ofthe product, in order to increase the solubility of (VIIb).

In yet a further aspect of the invention there is provided a method of preparing compound (VIIIb), its mirror image enantiomer or a mixture of such enantiomers, comprising reacting (–)-2-azabicyclo[2.2.1]hept-5-en-3-one (IX), its mirror image enantiomer or a mixture of such enantiomers, with one or more equivalents of an acid and one or more equivalents of water. Preferred acids are those with pKa less than two, most preferred are acids that give directlythe salts (VIIIb) described above, e.g. induding methanesulphonic acid and toluenesulphonic acid.

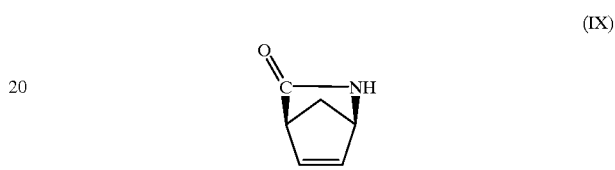

The reaction temperature can vary between 10° C. and 120° C., but is most preferably between 30° C. and 70° C.

The choice of solvent for this hydrolysis reaction can be quite varied, ranging from water to hydrocarbon solvents. Tne preferred solventis the one that will be used in thesubsequent reduction step. In this case, intermediate (VIII or VIIIa or VIIIb) can be used directly, without isolation.

Compound (VIII) and the salts (VIIIa) are prepared from the salt (VIIIb) by contacting it with a base and isolating the product by precipitation, crystallization, evaporation, etc. as is known to those skilled in the art. Almost any base with pKa greater than 3.5 can be used to make (VIII). The salt (VIIIa) must be prepared by contacting (VIIIb) with a base containing (W+). For example, the sodium salt can be prepared by contacting (VIIIb) with about two equivalents of the base sodium hydroxide.

In the present invention, it is also possible to easily remove color and impurities from the salt of intermediate (VIII) by washing it in the reactor (U.S. Pat. No. 4,734,194 Mar. 29, 1988)). Underthe protocol exemplified hereinafter, the toluenesulphonate and methane-sulphonate salts are found to be of particular advantage in that they filter exceptionally quickly.

As a further extension of the present invention, the sulphonic acid salt of comoound (VIII), its mirror image enantiomer or a mixture of such enantiomers, is prepared by performing an oxidative hydrolysis reaction on the Diels-Alder adduct between cyclopentadiene and an alkyl or aryi sulphonyl cyanide (X).

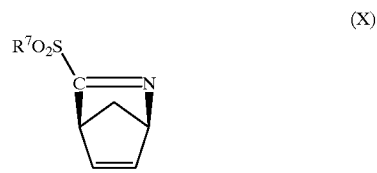

wherein $R^7$ is $C_{1-6}$ alkyl or aryl, its mirror image enantiomer or a mixture of such enantiomers. Preferred is where $R^7$ is methyl, phenyl, or tolyl. Most preferred is tolyl.

The literature (J. C. Jagt and A. M. vanLeusen, *J. Org. Chem.* 1974, 39, 564-566) teaches that the Diels-Alder adduct (X) is a particularly convenient precursor to the lactam (IX) by a hydrolysis reaction. Thus, by the application of an oxidative hydrolysis reaction to Diels-Alder adduct (X), compound (VIIIb) in its further preferred form can be obtained directly, and a step is saved in the overall process to prepare compound (VIIIb).

The oxidative hydrolysis reaction is accomplished by contacting Diels-Ader adduct (X) with at least one equivalent of water, at least one equivalent of an oxidizing agent, and preferably a catalytic amount of an acid.

The choice of solvent can be quite varied. It is preferable to use a solvent that poses a low hazard when combined with the oxidizing agent. Most preferred is to use water as both solvent and hydrolytic agent.

Suitable oxidizing agents are those that do not oxidize a double bond. Preferred are peroxides, most preferred is hydrogen peroxide. One to five equivalents of the oxidizing agent can be used.

In the preferred embodiment where a catalytic amount of acid is used, any acid of pKa less than 3 can be used, but it is preferred that the acid used be the same as the salt of compound (VIIIb) that is formed from the Diels-Alder adduct (VIIIb). For example, if R=tolyl in the adduct (X), the oxidative hydrolysis gives the toiuenesulphonate salt of compound (VIIIb). In this case, toluenesulphonic acid would be the preferred acid. If R=methyl in the adduct (X), the preferred acid would be methanesulphonic acid, etc. The amount of acid catalyst can range from 0 to 50 mol c/o relative to the DieisAlder adduct (X).

All of the structures shown above are intended to represent the racemate in addition to the single enantiomer depicted. Thus, the present invention is intended to encompass both the racernates and the pure enantiomers, substantially free of theirmirror-imageisomers.

A compound of formula (I) may be converted into a pharmaceutically acceptable ester by reaction with an appropriate esterifyi ng agent, e.g. an acd halide or anhydri de. The compound of formula (I) including esters thereof, may be converted into pharmaceutically acceptable salts thereof in conventional manner. e.g. by treatment with an appropriate acid. An esteror salt of an ester of formula (I) may be converted into the parent compound, e.g. by hydrolysis.

The following Examples are intended for illustration only and are not intended to limit the scope of the invention in anyway. The term active ingredient as used in the examples means a compound of formrula (I) or a pharmaceutically acceptable derivative thereof.

EXAMPLE A

Tablet Formulations

The following formulations A and B were prepared by wet granulation of the ingredients with a solution of povidone, followed by addition of magnesium stearate and compression

|  | mg/tablet | mg/tablet |
|---|---|---|
| Formulation A |  |  |
| (a) Active ingredient | 250 | 250 |
| (b) Lactose B.P. | 210 | 26 |
| (c) Povidone B.P. | 15 | 9 |
| (d) Sodium Starch Glycollate | 20 | 12 |
| (e) Magnesium Stearate | 5 | 3 |
|  | 500 | 300 |

-continued

|  | mg/tablet | mg/tablet |
|---|---|---|
| Formulation B |  |  |
| (a) Active ingredient | 250 | 250 |
| (b) Lactose | 150 | — |
| (c) Avicel PH 101 | 60 | 26 |
| (d) Povidone B.P. | 15 | 9 |
| (e) Sodium Starch Glycollate | 20 | 12 |
| (f) Magnesium Stearate | 5 | 3 |
|  | 500 | 300 |
| Formulation C. |  |  |
| Active ingredient | 100 |  |
| Lactose | 200 |  |
| Starch | 50 |  |
| Povidone | 5 |  |
| Magnesium stearate | 4 |  |
|  | 359 |  |

The following formulations, D and E, were prepared by direct compression of the admixed ingredients. The lactose used in formulation E was of the direct compression type (Dairy Crest—"Zeparox").

|  | mg/tablet |
|---|---|
| Formulation D |  |
| Active Ingredient | 250 |
| Pregelatinised Starch NF15 | 150 |
|  | 400 |
| Formulation E |  |
| Active ingredient | 250 |
| Lactose | 150 |
| Avicel | 100 |
|  | 500 |

Formulation F (Controlled Release Formulation)

The formulation was prepared by wet granulation of the ingredients (below) with a solution of povidone followed bythe addition of magnesium stearate and compression.

|  | mg/tablet |
|---|---|
| (a) Active Ingredient | 500 |
| (b) Hydroxypropylmethylcellulose (Methocel K4M Premium) | 112 |
| (c) Lactose B.P. | 53 |
| (d) Povidone B.P.C. | 28 |
| (e) Magnesium Stearate | 7 |
|  | 700 |

EXAMPLE B

Capsule Formulations

Formulation A

A capsule formulation was prepared by admixing the ingredients of Formulation D in Example 1 above and filling into a two-art hard gelatin capsule. Formulation B (infra) was prepared in a similar manner.

|  | mg/capsule |
| --- | --- |
| Formulation B | |
| (a) Active ingredient | 250 |
| (b) Lactose B.P. | 143 |
| (c) Sodium Starch Glycollate | 25 |
| (d) Magnesium Stearate | 2 |
| | 420 |
| Formulation C | |
| (a) Active ingredient | 250 |
| (b) Macrogol 4000 BP | 350 |
| | 600 |

Capsules were prepared by melting the macrogol 4000 BP, dispersing the active ingredient in the melt and filling the melt into a two-part hard gelatin capsule.

| Formulation D | mg/capsule |
| --- | --- |
| Active ingredient | 250 |
| Lecithin | 100 |
| Arachis Oil | 100 |
| | 450 |

Capsules were prepared by dispersing the active ingredient in the lecithin and arachis oil and filling the dispersion into soft, elastic gelatin capsules.
Formulation E (Controlled Release Capsule)

The following controlled release capsule formulation was prepared by extruding ingredients a, b and c using an extruder, followed by spheronisation of the extrudate and drying. The dried pellets were then coated with release-controlling membrane (d) and filled into a two-piece, hard gelatin capsule.

|  | mg/capsule |
| --- | --- |
| (a) Active Ingredient | 250 |
| (b) Microcrystalline Cellulose | 125 |
| (c) Lactose BP | 125 |
| (d) Ethyl Cellulose | 13 |
| | 513 |

EXAMPLE C
Injectable Formulation

| Formulation A | |
| --- | --- |
| Active ingredient | 0.200 g |
| Hydrochloric acid solution, 0.1M | q.s. to pH 4.0 to 7.0 |
| Sodium hydroxide solution, 0.1M | q.s. to pH 4.0 to 7.0 |
| Sterile water | q.s. to 10 ml |

The active ingredient was dissolved in most of the water (35-40° C.) and the pH adjusted to between 4.0 and 7.0 with the hydrochloric acid or the sodium hydroxide as appropriate. The batch was then made up to volume with the water and filtered through a sterile micropore filter into a sterile 10 ml amber glass vial (type 1) and sealedwith sterile closures and overseals

| Formulation B | |
| --- | --- |
| Active ingredient | 0.125 g |
| Sterile, pyrogen-free, pH 7 phosphate buffer, | q.s. to 25 ml |

EXAMPLE D

| Intramuscular injection | |
| --- | --- |
| Active Ingredient | 0.20 g |
| Benzyl Alcohol | 0.10 g |
| Glycofurol | 1.45 g |
| Water for Injection | q.s. to 3.00 ml |

The active ingredient was dissolved in the glycofurol. The benzyl alcohol was then added and dissolved, and water added to 3 ml. The mixture was then filtered through a sterile micropore filter and sealed in sterile 3 ml amber glass vials (type 1).

EXAMPLE E

| Syrup | |
| --- | --- |
| Active ingredient | 0.2500 g |
| Sorbitol Solution | 1.5000 g |
| Glycerol | 2.0000 g |
| Sodium Benzoate | 0.0050 g |
| Flavour, Peach 17.42.3169 | 0.0125 ml |
| Purified Water | q.s. to 5.0000 ml |

The active ingredient was dissolved in a mixture of the glycerol and most of the purified water. An aqueous solution of the sodium benzoate was then added to the solution, followed by addition of the sorbitol solution and finally the flavour. The volume was made up with purified water and mixed well.

EXAMPLE F

| Suppository | |
| --- | --- |
| | mg/suppository |
| Active Ingredient (631 m)* | 250 |
| Hard Fat, BP (Witepsol H15-Dynamit Nobel) | 1770 |
| | 2020 |

The active ingredient was used as a powder wherein at least 90% of the particles were of 63 lm diameter or less.

*The active ingredientwas used asa powder wherein at least 90% of the particles were of 63 lm diameter or less.

One-fifth of the Witepsol H15 was melted in a steamiacketed pan at 45° C. maximum. The active ingredient was sifted through a 200 lm sieve and added to the molten base with mixing, using a silverson fitted with a cutting head, until a smooth dispersion was achieved. Maintaining the mixture at 45° C., the remaining Witepsol H15was added to the suspension and stirred to ensure a homogeneous mix.

The entire suspension was passed through a 250 lm stainless steel screen and, with continuous stirring, was allowed to cool to 40° C. At a temperature of 38° C. to 40° C., 2.02 g of the mixture was filled into suitable, 2 ml plastic moulds. The suppositories were allowed to cool to room temperature

EXAMPLE G

Pessaries

| | mg/pessary |
|---|---|
| Active ingredient (631 m) | 250 |
| Anhydrate Dextrose | 380 |
| Potato Starch | 363 |
| Magnesium Stearate | 7 |
| | 1000 |

The above ingredients were mixed directly and pessaries prepared by direct compression of the resulting mixture
Antiviral Testing Human cytomegalovirus (HCMV) is assayed in monolayers of MRCS cells (human embryonic lung) in multiwell trays. Activity of compounds is determined in the plaque reduction assay, in which a cell monolayer is infected with a suspension of HCMV. A range of concentrations of the compound to be tested (of known moiarity) is then incorporated into the carboxymethyl cellulose overlay. Plaque numbers of each concentration are expressed as percentage of the control and a dose-response curve is drawn. From this curve the 50% inhibitory concentration ($IC_{50}$) is estimated.

Anti-HCMV Activity

| Compound | $IC_{50}$ ($\mu M$) |
|---|---|
| Ex. 22 | 3.1 |
| Ex. 23 | 2.8 |

Toxicity Testing

Compounds of formula (I) were tested fortoxicity in human bon marrow progenitor cells, in vitro, by the method of Dornsife, R. E. et at., 1991, Antimicrob. Agents Chemother., 35: 322-328. Three separate assays were performed using marrow from three different donors.

Cell Toxicity

| | $I_{50}$ ($\mu M$)* | |
|---|---|---|
| Compound | CFU-GM | BFU-E |
| Ex. 22 | 34 ± 14 | >>50 |
| Ex. 23 | 14 ± 1 | 55 ± 15 |
| 2'-CDG | 0.4 ± 0.3 | 4 ± 2 |

*50% inhibition of bone marrow progenitor cells.

EXAMPLE 1
(−)-(1S, 4R)-4-Amino-2-cyclopentene-1-carboxylic acid methanesulfonate A solution of (−)-2-azabicyclo[2.2.1]hept-5-en-3one (97.45 g, 0.8929 mol, Enzymatix Ltd.) in tetrahydrofuran (500 mL) was filtered and warmed to 35° C. A solution of methanesulfonic acid (63.7 mL, 0.9817 mol) in water (24.1 mL, 1.34 mol) was added over the course of 1.5 hours such that the ensuing exotherm did not exceed 45° C. The resulting slurry was heated at 60° C. for three hours, then allowed to coot to room temperature over the course of 15 hours. The slurry was filtered and the cake washed twice with anhydrous tetrahydrofuran (200 mL). An analytical sample of the wet cake was removed and dried to give the title compound as a white solid (1.264 g); m.p. 167-169.2° C.; $^1$H-NMR (DMSO-$d_6$) δ: 12.6 (brs, 1H, $CO_2H$), 8.04 (br s, 3H, $NH_3^-$), 6.10 (dt, J=5.6, 2.0, 2.0 Hz, 1H, vinyl), 5.85 (dt, J=5.3, 2.3, 2.3 Hz, 1H, vinyl), 4.19 (br s, w½=20 Hz, 1H, allytic H), 3.61 (m, w½=22Hz, 1H, altylic H), 2.53 (quintet, J=5.3 Hz (overlapping with DMSO peak), ½ $CH_2$), 2.39 (s, 3H), $CH_3SO_3H$), 1.93 (dt, J=6.7, 6.7, 13.7 Hz, 1H, ½ $CH_2$); $[\alpha]^{20}_{589}$-83.8°, $[\alpha]^{20}_{578}$-87.4°, $[\alpha]^{20}_{546}$-101.2°, $[\alpha]^{20}_{436}$-186.7°, $[\alpha]^{20}_{365}$-316.2° (c=1.42, methanol); CI-MS ($CH_4$): 128(M+1); EI-MS; 127(M).

Anal. Calcd. for $C_7H_{13}NO_5S$: C, 37.66, H. 5.87; N, 6.27; S, 14.36. Found: C, 37.65; H, 5.88; N, 6.30; S, 14.44.

The remaining wet cake was used directly in the following example.

EXAMPLE 2
(−)-(1S, 4R)-4-Amino-2-cyclopentene-1-methanol

The tetrahydrofuran-wet cake of (−)-(1S, 4R)-4amino-2-cyclopetene 1-carboxylic acid methanesulfonate prepared in the above example was suspended in dry tetrahydrofuran (400 mL) and transferred via cannula to a rapidly stirring solution of lithium aluminum hydride in tetrahydrofuran (1.0 molar, 1600 mL, 1.6 mol, Aldrich) cooled in an ice/acetone bath. The rate of transfer was limited to control the rate of gas evolution and to keep the temperature between 0° and 10° C. (total time of addition 1.5 hours). The resulting mixture was warmed to reflux over the course of two hours, then refluxed for 16 hours.

Approximately 16 L of solventwas removed by distillation, the resulting slurry was cooled in an ice-acetone bath, then treated with diethyl ether (dry, 1 L) and sodium fluoride (403.3 g, 9.605 mol, Aldrich). Water (86 mL, 4.8 mol) was added slowly at such a rate (three hours) that the temperature was kept below 5° C. and the hydrogen evolution was moderated. The resulting slurry was filtered and the cake washed with tetrahydrofuran (200 mL), then 7% water-tetrahydroiuran (500 mL). Quantitative HPLC analysis (see Example 3, below) of the filtrate showed it to contain 60.04 g of the title compound. The cake was reslurried in 7% water-tetrahydrofuran (1 L) for a half hour, filtered, and washed with 7% water-tetrahydrofuran (400 mL), then 10% water-tetrahydrofuran (300 ml). Quantitative HPLC analysis (see Example 3, below) of the filtrate showed it to contain 26.70 g of the title compound. The cake was reslurried in methanol (1 L) for 16 hours, filtered, and washed with methanol (500 mL). Quantitative HPLC analysis (see Example 3, below) of the filtrate showed itto contain 4.09 g of the title compound. The total yield of thetitle compound was thus 9.83 g, 0.8027 mol. or 90.5% of theoretical yield corrected for the analytical sample removed.

EXAMPLE 3
Analysis of (−)-(1S, 4R)-4Amino-2-cyclonentene-1-methanol and its enantiomer, (+)-(1R, 4S)-4-amino-2-cyclooentene- 1-methanol Samples of the title compounds were characterized by the method of Bruckner, H., Wittner, R., and Godel, H., "Automated Enantioseparation of Amino Acids by Derivatization with o-Phthaldialdehyde and N-Acylated Cysteines", J. Chrom., 476(1989) 73-82. Using o-phthaldialdehyde and N-acetyl-L-cysteine as derivatizing reagents. The chromatographic separation used an Optima II ODS 100×4.5 mm, 3 lim column (III Supplies Co., Meriden, Conn.) and gradient elution at 0.9 mL/min using initially 100% sodium acetate buffer, 40 mM, pH 6.5, with a linear ramp to 18% acetonitriie over 15 minutes and a subsequent hold at 18% acetonitrile for 15 minutes. Detection was at 338 nm. Samples were dissolved in 0.1 molar borate buffer, pH 10.4. The identity and purity of the samples was established by comparison with authentic standards (see EP 434450 (Jun. 26, 1991)). The retention time of the (1S, RS) isomer was about 21 minutes. The retention time of the (1R, 4S) isomer was about 22 minutes.

EXAMPLE 4

(−)-(1R, 4S)-tert-Butyl N-[4-hydroxvmethyl)-2-cyclogoenten-1-yl]carbamate

The first filtrate of Example 2 containing (−)-(1S, 4R-amino-2-cycopentene-1-methanol was cooled in aniceacetone bath and treated with di-tert-butyl dicarbonate (199.42 g, 0.9265 mol, Aldrich). The mixture was concentrated under vacuum to a volume of 300 mL, and added to the second filtrate of Example 2 that had meanwhile been cooled in an ice-acetone bath. The mixture was allowed to stir and warm to room temperature over the course of 18 hours, during which time gas evolved and a clear solution formed. This solution was combined with the last filtrate of Example 2 which had been evaporated under vacuum to a mixture of oil and solids. The resulting solution was evaporated under vacuum to an oil. The oil was partitioned between ethyl acetate (300 mL) and phosphate buffer (100 mL of 1.5 molar potassium dihydrogen phosphate adjusted to pH 7.0 with 50% sodium hydlroxide-water). The phases were separated, the aqueous phase was reextracted twice with ethyl acetate (200 mL). The organic phases were dried over sodium sulfate and filtered through silica gel (50 g.). The solvent was removed under vacuum to give an oil (220.78 g), which was taken up in hexanes (300 mL). A minimum amount of ethyl acetate (about 50 mL) was added in order to dissolve the oil, and the solution was set to crystallize over the course of three days. The crystals were filtered off, washed with 20% ethyl acetate/hexanes, and dried by suction to a constantweight (156.1 g, 0.732 mol, 82.6% of theory) of the title compound; m.p. 73-73.7° C.; $^1$H-NMR (DMSO-$d_6$) 5: 6.72 (d, J=7.9 Hz, 1H, NH), 5.80 and 5.60 (two m, 2H, CH=CH), 4.59 (t, J=5.2 Hz, 1H, OH), 4.45 (m, 1H, CHN), 3.35 (m, overlapping $H_2O$, $CH_2O$), 2.60 (m, 1H, CH), 2.30 (m, 1H, ½ $CH_2$), 1.40 (s, 9H, $C(CH_3)_3$), 1.2 (m, 1H, ½$CH_2$); $[\alpha]^{20}_{589}$-2.78°, $[\alpha]^{20}_{578}$-2.84°, $[\alpha]^{20}_{546}$-3.6°, $[\alpha]^{20}_{436}$-3.39°, $[\alpha]^{20}_{365}$-0.95° (c=5.07, methanol); Cl-MS ($CH_4$) 214 (M+1); TLC (silica, 10% methanol-chloroform, iodine visualization), $R_f$=0.51.

Anal. Calcd. for $C_{11}H_{19}O_{13}N$: C, 61.95; H, 8.98, N, 6.57. Found: C, 61.87; H, 8.96; N, 6.59.

An additional 10.14 g of crystalline material was recovered from the mother liquor by crystallization and chromatography, bringing the total yield to 166.24 g (0.780 mol, 87.9% of theory from the lactam starting material of Example 1).

It was also found convenient to prepare the title compound directly from 2-azabicyclo [2.2.1] hept-S-en-3-one, either racemic or the (−) enantiomer, as follows. (−)2-Azabicyclo [2.2.1] hept-S-en-3-one (6.00 g, 55.0 mmol) in anhydroustetrahydrofuran (30 mL) was warmed to 34° C. and stirred while methanesulfonic acid (3.6 mL, 55 mmol) and water (0.99 mL, 55 mmol) were added dropwise over 10 minutes. An exotherm of 10° C. was observed within 5 minutes and a crystalline solid began to precipitate. The mixture was refluxed (oil bath at 74° C.) for 2.5 hours. The mixture was cooled to −10° C. and a solution of lithium aluminum hydride (1.0 M intetrahydrofuran, 100 mL) added. The first 15 mL was added over 10 minutes and an exotherm of 7° C. noted. The remaining 85 mL was added rapidly with no further exotherm noted. The mixture was brought to reflux over 30 minutes and reflux continued for 18hours. The mixture was cooled to 25° C.and sodium fluoride (25.2 g, 0.600 mole) was added and, after stirring for 30 minutes water (5.3 mL) was added dropwise over 10 minutes to the cooled (0° C.) mixture. The mixture was stirred for 30 minutes at 25° C. and di-tert-butyl dicarbonate (12.6 mL, 55.0 mmol) was added. This mixture was stirred for 16 hours, filtered, and the cake triturated with ethyl acetate (2×50 mL). The combined filteratewash was washed with water (20 mL), dried ($Na_2SO_4$), evaporated, and the residual syrup crystallized from ethyl acetate:hexanes/1:2 (30 mL) to give title compound as white crystals (10.32 g, 88%), identical in properties to the above-described sample.

EXAMPLE 5

(−)-(1R, 2S, 3R, 4R)-tert-Butyl N-[2,3-dihydroxy-4-(hydroxymethyl)-1-cyclopentyl] carbamate To a mixture of N-methyl morpholine-N-oxide (146.2 g, 60% in water, 0.749 mol) and osmium tetroxide (9.75 g, 2.5% in tert-butanol, 0.959 mmol) in acetone (1 L) stirring at −8° C. in an ice-acetone bath was added in one portion (−)-(1R, 4S)-tert-butyl N-[4-hydroxymethyl)-2-cyclopenten-1-yl] carbamate (152.10 g, 0.7132 mol, from the preceding Example). The resulting mixture was allowed to warm to room temperature over 16 hours, during which time it became homogeneous. More osmium tetroxide was added (2 602 g, 0.256 mmol), and the solution was stirred at 20° C. for four hours, then 40° for two hours, at which time the reaction was judged complete by TLC (silica, 10% methanol-chloroform, visualization with iodine followed by vanillin char, starting material: $R_1$=0.51 products: $R_f$=0.22, (2S, 3R)-isomer, and $R_f$20.36, (2R, 3S)-isomer). The ratio of (2S, 3R)/(2R, 3S) isomers was about 73:27 as judged by $^1$H-NMR and TLC. Water (75 mL) was added, fol lowed by chloroform (2 L). The resulting twophase mixture was cooled in an ice bath, and with very gentle agitation (to discourage phase mixing), anhydrous copper sulfate (457.8 g, Alfa) was added in several portions. The resulting slurry was allowed to stir at room temperature about 16 hours, thenwasfiltered with filter aids (Celite 545 and 512). The cake was washed with tetrahydrofuran (6 L) until no more product eluted. The filtrate was evaporated under vacuum to a dark oil substantially free of N-methyl morpholine. The oil was filtered through silica gel (300 g), and eluted with tetrahydrofuran (3 L) until all of the productwas eluted. The eluate was concentrated to 200 mL, and hexanes (about 300 mL) was added. Crystallization began spontaneously, and was allowed to continue at −5° C. for about 16 hours. The crystals were recovered by filtration, washed sparingly with 50% ethyl acetatlhexanes, and dried by suction to a constant weight (105.78 g, 0.428 mol, 60.0% of theoretical). Recrystallization from refluxing ethyl acetate (200 mL) provided the title compound as white crystals (93.85 g, 0.3795 mol, 53.2% of theoretical); m.p. 115.8-117°; $^1$H-NMR (DMSO-$d_6$) δ: 6.71 (br d, J=7.4 Hz, 1H, NH), 4.52 (t, J=5.2 Hz, 1H, $CH_2OH$), 4.43 (d, J=5.1 Hz, 1H, CHOH), 4.31 (d, J=4.9 Hz, 1H, CHOH), 3.54-3.41 (overlapping multiplet, 3H, CHN and CHOH), 3.34 (m, overlapping with HOD, w½=20 Hz, $CH_2OH$), 19.9 (dt, J=12.5, 6.8, 6.8 Hz, 1H, $HOCH_2(CH)$, 1.85 (br. m, w½$CH_2$, 1.39 (s, 9H, $C(CH_3)_3$), 0.98 (dt, J=12.4, 7.8, 7.8 Hz, 1H, ½$CH_2$); $[\alpha]^{20}_{589}$-8.08°, $[\alpha]^{20}_{578}$-8.57°, $[\alpha]^{20}_{546}$-9.95°, $[\alpha]^{20}_{436}$-18.22, $[\alpha]^{20}_{365}$-29.36° (c=1.02, methanol); Cl-MS (CH$_4$) 248 (M+1).

Anal. Calcd. for $C_{11}H_{21}O_5N$: C, 53.43; H, 8.56; N, 5.66. Found: C, 53.45; H 8.58; N, 5.69.

A sample of the (-)-(2R, 3S)-isomer (25.60 g) was obtained from the mother liquors by fractional crystallization from ethyl acetate; m.p. 106-107.2° C; $^1$H-NMR (DMSO-d$_6$) δ: 5.93 (br d, J=7.6 Hz, 1H, NH), 4.77 (d, J=4.9 Hz, 1H, CHOH), 4.58 (d, J=4.1 Hz, 1H, CHOH),4.35 (brt, t, w½=15 Hz, 1H, CH$_2$OH), 3.89 (br s, w½=10 Hz, 1H, OCH, 3.73 (br s, 2H, OCH, NCH), 3.50 (br m, w½=20 Hz, 1H, ½OCH$_2$), 3.38 (br m, obscured by HOD, ½OCH$_2$), 1.90 (m, w½=24 Hz, 2H, OCH$_2$CH, ½CH$_2$), 1.38 (s, 9H, C(CH$_3$)$_3$), 1.27 (m, 1H, ½CH$_2$); $[\alpha]^{20}_{589}$-7.92°, $[\alpha]^{20}_{578}$-8.14°, $[\alpha]^{20}_{546}$-9.05°, $[\alpha]^{20}_{436}$-14.81°, $[\alpha]^{20}_{365}$-21.19° (c=1.36, methanol); Cl-MS (CH$_4$), 248 (M+1).

Anal. Calcd. for $C_{11}H_{21}O_5N$, 0.05 H$_2$O: C, 53.23; H, 8.57; N, 5.64. Found: C, 53.20; H, 8.55; N, 5.61.

EXAMPLE 6

(-)-(6aR, 8R, 9S, 9aR)-tert-Butyl N-(hexahydro-9-hydroxy-2,2,4,4-tetraisopropyl cyclopenta [f]-1,3,5, 2,4-trioxadisilocin-8yl) carbamate The product of the preceding Example, (-)-(1R, 2S, 3R, 4R)-tert-butyl N-[2,3-dihydroxy-4-(hydroxymethyl)-1-cyclopentyl] carbamate (92.97 g, 0.3760 mol) and imidazole (103.0 g, 1.513 mol, Aldrich) were dissolved in dry N,N-dimethylformamide (200 mL, Aldrich) and cooled to -7° C. in an ice-acetone bath. With rapid stirring, 1,3-dichloro-1, 1,3,3-tetraisopropyl disiloxane (121.2 g, 0.3842 mol, Cambridge, refractionated) was run in at once (about ½ minute), and immediately washed in with cyclohexane (10 mL). An immediate exotherm carried the temperature to 35° C., then subsided. At 10° C., the cooling bath was removed and the mixture was aLlowed to stir at room temperature for two days. The reaction mixture was partitioned between cyclohexane and ice water (200 mL each). The lower phase (pH=7) was extracted with two additional portions of cyclohexane (200 mL each), and each of the organic extractswas then washed in sequence with four portions of water(1 50 mL) and one portion of saturated aqueous sodium sulfate. The organic phases were dried over anhydrous sodium sulfate, then filtered and concentrated under vacuum to a volume of about 250 mL (slightly yellow sol utian), which was used directly in the following Example.

A sample of the title compound prepared similarly but purified by chromatography on silica get (eluted with 20% ethyl acetatehexanes) gave a colorless glass, which crystallized on standing with the following characteristics; m.p. 63.5-65.2° C; $^1$H-NMR (DMSO-d$_6$) δ: 6.96 (br d, J=4.8 Hz, 1H, NH), 4.24 (d, J=4.8 Hz, 1OH), 3.93 (dd, J=7.3, 5.5 Hz, 1H, NCH), 3.83 (dd, J=13, 2.7 Hz, 1H, OCH), 3.65 (q, J=4.7 Hz, 2H, CH$_2$O), 3.53 (br d,J~6 Hz, 1H, OCH), 2.09-1.80 (br m, 2H, CH and ½CH$_2$), 1.39 (s, 9H, C(CH$_3$)$_3$), 1.04 (m, w½=13 Hz, 29H, CH (CH$_3$)$_2$ and ½CH$_2$, obscured); $[\alpha]^{20}_{589}$-15.45°, $[\alpha]^{20}_{578}$-16.23°, $[\alpha]^{20}_{546}$-19.21°, $[\alpha]^{20}_{436}$-33.62°, $[\alpha]^{20}_{365}$-52.43° (c=0.779, methanol, corrected for 0.3 H$_2$O); Cl-MS (CH$_4$); 490 (M+1); TLC (silica, 20% ethyl acetate-hexanes, odine visualization) R$_f$=0.46.

Anal. Calcd. for $C_{23}H_{47}NO_6Si_2$·0.3H$_2$O: C, 55.79; H, 9.69; N, 2.83. Found: C, 55.81; H, 9.57; N, 2.83.

EXAMPLE 7

(-)-6aR, 8R, 95 9aR)-tert-Butyl N-(hexanydro-2,2, 4,4-tetraisopropyl-9-((phenoxythiocarbonvl) oxy)-cyclopenta [f]-1,3,5,2,4-trioxadisilocin-8-yl) carbamate The solution of (-)-(6aR, 8R, 9S, 9aR)-tert-butyl N-(hexahydro-9-hydroxy-2,2,4,4-tetraisopropylcyclopenta [f]-1,3,5,2,4-trioxadisilocin-8-yl) carbamate (0.3760 mol) in cyclohexane, obtained in the preceding Example was diluted to a total vol ume of 500 mL with cyclohexane. N-Hydroxysuccinimide (8.568 g, 74.45 mmol), and pyridine (33.2 mL, 0.410 mol) were added, then with rapid stirring, a solution of phenyl thionochloroformate (70.8 g, 0.410 mol) in cyclohexane(50 mL) was added dropwise over the course of 20 minutes. The resulting dark mixture was stirred for 16 hours at room temperature, then refluxed for four hours. Pyridine (7.1 mL, 88 mmol), then phenylthionochloroformate (15.09 g, 87.41 mmol) were added, and the mixture was refluxed forthree hours. Pyridine (5.0 mL, 62 mmol) ana phenylthionochloroformate (9.903 g, 57.37 mmol) were added, and the mixture was refluxed an additional 3.5 hours, at which time it was judged complete by TLC (silica, 20% ethyl acetatehexanes, visualization with iodine followed by vanillin char; starting material: R$_f$20.46, product: R$_f$20.49). The mixture was distilled to a volume of about 400 mL, cooled to room temperature, then filtered through a bed of filter aid (1 cm, Celite 545) under a dry nitrogen atmosphere. The resulting cake of pyridine hydrochloride was washed with cyclohexane (200 mL), to give a solution of the title compound in cyclohexane.

A sample prepared similarly, but purified by chromatography on silica gel (eluted with 10% ethyl acetate-hexanes) gave a colorless oil with the following characteristics; 1H-NMR DMSO-d$_6$), δ: 7.56–7.28 (m, 4H, o- and m-ArH), 7.11 (br d, J=7.3 Hz, 2H, NH and p-ArH), 5.49 (dd, J=5.3, 3.3 Hz, 1H, COCH), 4.33 (br m, w½=20 Hz, 1H, NCH), 3.88 (m, 2H, ½CH$_2$O and OCH), 3.71 (br dd J~12, 3 Hz, 1H, ½OCH$_2$), 2.11–1.88 (br m, 2H, ½CH$_2$ and CH), 1.40 (s, 9H, C(CH$_3$)$_3$, 1.05 (d, J=4.9 Hz, overlapping with multiplet, 29H, ½CH$_2$+4CH (CH$_3$)$_2$); $[\alpha]^{20}_{589}$-3.17°, $[\alpha]^{20}_{578}$-33.1°, $[\alpha^{20}_{546}$-37.4°, $[\alpha]^{20}_{436}$-51.3°, $[\alpha]^{20}_{365}$-71.4°(c=1.19, methanol, corrected for 0.15 methylene chloride, 0.10 ethyl acetate and 0.10 water);

Anal. Calcd for $C_{30}H_{51}O_7NSI_2S$·0.15CH$_2$cl$_2$-O0.10 C$_\alpha$H$_8$O$_2$·0.10H$_2$O: C, 56.51; H, 8.12; N, 2.16; S, 4.94. Found: C, 56.77; H, 8341; N, 2.19; S, 4.98.

EXAMPLE 8

(-)-(6aR, 8R, 9aS)-tert-Butyl N-(hexahydro-2,2,4,4-tetraisoproyiycyclooerta [f]-1,3,5,2,4-trioxadisilocin-8-yl) carbamate The cyclohexane solution of (6aR, 8R, 9S, 9aR)-tert-butyl N-hexahydro-2,2,4,4-tetraisopropyl-9-[(phenoxythiocarbonyl)oxy]-cyclopenta [f]-1,3,5,2,4-trioxadisilocin-8yl) carbamate (0.3760 mol) prepared in the previous Example was degassed under a nitrogen atmosphere. Tributyltin hydride (207.4 g, 0.713 mol) and 2,2'-azo bis (2-methylpropionitrile) (12.79 g, 77.86 mmol) were added, the degassing was repeated, and the black solution was refluxed for four hours, during which time it turned to an amber color, and the reaction was judged complete by TLC (silica, 20% ethyl acetate-hexanes, visualized with iodine followed by vanillin char, starting material; R$_f$20.49, product: R$_f$0.36, white spot). The reaction solution was cooled to room temperature and added to 5% ammonium hydroxide-water (500 mL). The lower (aqueous) phase was extracted with two portions of hexane (200 mL each), and each of the organic extracts was then washed in sequence with 5% aqueous ammonia (two 500 mL portions, to remove phenol) water (500 mL), and saturated aqueous sodium sulfate (200 mL). The combined organic extracts were dried over sodium sulfate, then applied to a column of silica gel (about 1 Kg), which was eiuted with hexanes (1 L), 5% ethyl acetate-hexanes (1 L), 20% ethyl acetate-hexanes (1 L) and ethyl acetate. All fractions containing productwere evaporated to an amberoil (322.5 g). This was further purified by chromatography on two columns of silica gel (1 Kg each, eluted with an ethyl acetate-hexanes gradient) giving the title compound in two portions as an oil (74.32 g and 73.82 g, respectively, total 148.14 g, 0.313 mol, 83.2% of theoretical from the triol product of Example 5). A sample prepared similarly, but taken as the central fraction of the chromatography gave a colorless, crystallizing glass with the following characteristics: m.p. 66-67.0° C.; $^1$H-NMR (DMSO-$d_6$); δ; 6.93 (br d, J=6 Hz, 1H, NH), 4.22 (q, J=6.8 Hz, 1H, NCH), 3.84 (dd, J=3.1 11.5 Hz, 2H, $CH_2O$), 3.61 (dd, J=6.5, 9Hz, 1H, OCH), 1.91–1.73 (br m, 4H, CH, ½$CH_2$, $CH_2$), 1.38 (s, 9H, C($CH_3$)$_3$), 1.02 (m, w½=21 Hz, 29H, 4CH ($CH_3$)$_2$ and ½$CH_2$, obscured; $[\alpha]^{20}_{589}$-2.78°, $[\alpha]^{20}_{578}$-2.84°, $[\alpha]^{20}_{546}$-3.06°, $[\alpha]^{20}_{436}$-3.39°, $[\alpha]^{20}_{365}$-0.95° (c=5.07, methanol); Cl-MS ($CH_4$); 474 (M+1).

Anal. Calcd. for $C_{23}H_{47}NO_5Si_2$ C, 58.31; H, 10.00; N, 2.96. Found: C, 58.33; H, 10.00; N, 2.97.

EXAMPLE 9

(+)-(!R, 3S, 4R)-tert-Butyl N-[-hydroxy-4-(hydroxymethyl)-1-cyclopentyl] carbamate To a solution of (−)-(6aR, 8R, 9aS)-tert-butyl N-hexahydro-2 ,2,4,4-tetraisopropylcyclopenta ([f]-1,3,5,2, 4-trioxadisilocin-8-yl) carbamate (74.32 g, 0. 1569 mol, corresponding to the first portion of product in the above Exampie) in tetrahydrofuran (300 mL) was added tetraethyl ammonium fluoride hydrate [24.62 g9 about 0.15 mol, Aldrich). The lumps of solid were broken up, the mixture was degassed (nitrogen), then refluxed for 45 minutes. After cooling to room temperature, the reaction mixture was appilied to a column of silica gel (200 g) and eluted with tetrahydrofuran (3 L). The eluate was concentrated under vacuum to an amber oil, which was taken up in hexanes (150 mL). Crystallization began spontaneously, and was allowed to continue at −5° for two days. The crystals of crude title compound were collected by filtration, washed sparingly with 10% ethyl acetate-hexanes, and dried bysuctionto constantweight (25.08 g, 0.1084 mol). The procedure was repeated on the second portion of product from the above Example (73.829, 0.1558 mol), giving additional crude title compound (27.28 g, 0.1180 mol). The two portions of crude title compound were combined and recrystallized from boiling ethyl acetate (250 mL), giving white crystals of the title compound (46.67 g., 0.2018 mol, 53.7% of theoretical from the triol product of Example 5) having the following characteristics: m.p. 126-127.9° C.; 1H-NMR (DMSO-$d_6$), δ: 6.75 (br d, J=7.8 Hz, 1H, NH), 4,49 (t, J=4.5 Hz, CH2OH), overlapping 4.47 (d, J=4.3 Hz, CHOH) with total integration of 2H, 3.80-3.93 (m, 2H, CHN and CHOH), 3.34 (m, w½ 20 Hz, $CH_2$OH), 2.25 (dt, 1H, $CHCH_2$), 1.79–1.63 (m, 2H, $CH_2$CHOH), 1.63–1.50 (m, 1H, ½$CH_2$), 1.38 (s, 9H, C($CH_3$)$_3$)$_3$), 1.11-0.96 (m, 1H, ½$CH_2$); Cl-MS ($CH_4$): 232(M+1).

Anal Calcd for $C_{11}H_{21}O_4N$: C, 57.12; H, 9.15; N, 6.06. Found: C, 57.07; H, 9.12; N, 6.08.

A chromatographically homogeneous sample of the title compound prepared similarly showed: $[\alpha]^{20}_{589}$+15.4°, $[\alpha]^{20}_{578}$+16.0°, $[\alpha]^{20}_{546}$+18.2°, $[\alpha]^{20}_{436}$+30.1°, $[\alpha]^{20}_{365}$+43.7°(c=0.51, methanol, corrected for 0.13 $H_2O$ solvation).

EXAMPLE 10

(+)-(1S, 2R, 4R)-Amino-2-(hydroxymethyl)-1-cyclopentanol

The product of the preceding Example, (+)-(1R, 3S, 4R)-tert-butyl N-[3-hydroxy-4-(hydroxymethyl)-1-cyclopentyl] carbamate (2.351 g, 10.17 mmol) was slurried in aqueous hydrochloric acid (1.0 molar. 25.4 mL, 25.4 mmol) and heated gently (60-83° C.) until a colorless solution formed, and the gas evolution subsided (about 15 minutes). The solution was allowed to cool to room temperature, then was concentrated under vacuum to a syrup, which was taken up in water(about 20 mL) and reconcentrated. The resulting syrup of hydrochloride salt was applied to a column of quaternary amine ion exchange resin (about 50 mL of Amberlite IRA-400, hydroxide form, washed to neutrality with water), and eluted with water (500 mL). The water was evaporated under vacuum, leaving the title compound as a colorless syrup (16.2 g). $^1$H-NMR (DMSO-$d_6$), δ: 3.90 (dt, J=474.7, 6.4 Hz, 1H, NCH), 3.47–3.23 (m, obscured by braod OH peak, ~3H, $CH_2O$ and CHO), 1.97 (dt, J=7.3, 7.3, 12.7 Hz, 1H, $CHCH_2OH$), 1.78 (br sextet, J=5 Hz, 1H, ½$CH_2$), 1.61 (m, w½=22 Hz, 1H, ½$CH_2$), 1.47 (m, w½=30 Hz, 1H, ½$CH_2$), 0.94 (dt, J=7.2, 7.2, 12.3 Hz, 1H, ½$CH_2$); $[\alpha]^{20}_{589}$+35.9°, $[\alpha]^{20}_{578}$+37.3°, $[\alpha]^{20}_{546}$30 42.3°, $[\alpha]^{20}_{436}$+69.9°, $[\alpha]^{20}_{365}$+103.0°, (c=2.49 methanol, corrected for 1.3 $H_2O$); Cl-MS ($CH_4$); 132 (M+1).

Anal. Calcd. for $C_6H_{13}O_2N$·1.3$H_2$: C, 46.62; H, 10.17; N, 9.06. Found: C, 46.61; H, 9.99; N, 8.93.

EXAMPLE 11

(±)cis-4-Amino-2-cyclopentene-1-carboxylic acid, 4-toluenesulfonate

A 500 mL, three neck flask with vertical joints was charged with (±)-2-azabicyclo [2.2.1] hept-5-en-3-one (48.66 g, 0.4459 mol, Cambridge), and equipped with a mechanical stirrer, thermometer with gas inlet adapter connected to the nitrogen supply, and a powder funnel. Tetrahydrofuran (200 mL, reagent grade) was added, and the stirrer started in order to dissolve the soiid An endotherm of 13° C. was noted. A gentle nitrogen sweep was applied from the inletadapter outthe powder funnel and 4-toluene sulfonic acid hydrate (93.52 g, 0.416 mol, 1.1 equv) was added, along with a small amount of the title compound as seed. The powder funnel was replaced by a reflux condenser, and the flask was immersed in an oil bath preequilibrated to 35° C. Within 10 minutes, crystallization began, foliowed by an exotherm peaking at 60° C. in another 15 minutes. Afterthe exotherm peaked, the bath was reset to 60-65° C., and the reaction mixture was heated two hours at 60-65° C. (internal), until a TLC of the supernatant liquid (silica, ethyl acetate eluent, iodine visualization) shows the absence of starting lactam against an authentic spot. The mixture was then cooled in an ice bath to ~5° C. A giass tube with a fritted end was connected via flexible tubing to a filter flask, in turn connected to a vacuum source. The condenser was removed from the flask containing the slurry, the stirrer was stopped, and with a nitrogen sweep from the gas inlet, the fritted end of the stick was pushed to the bottom of the flask under the agitator, Vacuum was applied until the liquid was completely removed, the solids were reslurried in drytetrahydrofuran (100 ML), andthefiltration operation was repeated. The resulting white solids were reslurried in curry tetrahydrofuran (200 mL), and the open neck was capped with a septum. The resulting slurryof the title compound was used directly in the following Example: an analytical sample was prepared similarly, except that it was dried first by suction then by the application of vacuum; m.p. 191-193° C.; 1H-NMR (DMSO-$d_6$), δ: 12.62 (br s, 1H, $CO_2H$), 7.93 (br s, 3H, $NH_3^+$), 7.47 and 7.11 (dd, 8.0 Hz, 2H each, Ar-H), 6.11 (dt, J=5.7, 1.9, 1.9, Hz, 1H, vinyl), 5.82 (dt, J=5.7, 2.8, 2.8 Hz, 1H vinyl), 4.20 (br m, w½=21 Hz, 1H, allylic H), 3.61 (br tt?, w½=21 Hz, 1H, allylic), 2.29 (s, 3H, CH$_3$), 2.50 (dt?, J=5.8, 5.8, 11.5 Hz, (overlapping DMSO peak), ½CH$_2$), 1.92 (dt, J=6.7, 6.7, 13.4 Hz, 1H, ½CH$_2$).

Anal. Calcd. for C$_{13}$H$_{17}$O$_5$N$_5$: C, 52.16; H, 5.72N, 4.68S, 10.71. Found: C, 52.16; H, 5.76; N, 4.66; S, 10.62.

EXAMPLE 12

(±)-cis-4-Amino-2-cyclopentene-1-methanol

A dry, 2 L, three-neck flask was equipped with a mechanical stirrer, thermometer with gas inlet adapter connected to the nitrogen supply, and septum. The flask was purged with nitrogen, immersed in an iceacetone bath, and lithium aluminum hydride solution in tetrahydrofuran (1.0 molar, 800 mL, 0.80 mol, Aldrich) was added via cannula. Dry tetrahydrofuran (2×15 mL) was used to rinse in the lithium aluminum hydride solution. When the solution had cooled to 0° C., the slurry of (±)-cis-4amino-2cyclopentene-1-carboxylic acid 4-toluenesulfonate salt in tetrahydrofuran prepared in the previous Example was cannulated in with good stirring, at such a rate as to keep the temperature less than 10° C. and moderate the hydrogen evolution (about one hour). The flask was rinsed with dry tetrahydrofuran (2×15 mL), and the septum was replaced with a reflux condenser. The resulting clear, light amber solution was slowly warmed to a gentle reflux over the course of two hours, at which point it became cioudy After refluxing overnight (16 hours), the heating bath was dropped, sodium fluoride (136.3 g, 3.25 mol, reagent grade powder) was added, and the condenser resetfor downward distillation. The mixture was distilled to a thin slurry (700 of distillate collected), then cooled in an ice bath. Diethyl ether (dry, 500 mL) was added, and the condenser was replaced by an addition funnel containing water (43 ml, 2.4 mol). The water was ad dec ery slowly (two hours), with care taken to control the rate of hydrogen evolution and maintain the temperature at 10±5° C. Meanwhile, water (54 mL) was added to the above recovered distillate, and sufficient additional tetrahydrofuran was added to bring the total volume to 900 ml (6% H$_2$O). The reaction mixture was filtered by suction, and the cake displace-washed with tetrahydrofuran (100 mL). Part of the 6% water-terrahydrofuran solution (300 mL)was used to slurry-wash the cake, which was then returned to tne reaction flask. The cake was triturated (25 minutes) in 6% water-tetrahydrofuran (400 mL), filtered, and displace-washed with 6% water-tetrahydrofuran (200 mL). The combined filtrates were concentrated to a paleyellow oil undervacuum (44.07 g, 67.8% by HPLC, see Example 3. The containing pure title compound, water, and a trace of tosylate salt, darkens rapidly under ambient conditions. It was immediately reacted to form the N-BCC derivative, a stable, crystalline solid, (see the following Example). The filter cake was returned to the flask and triturated in methanol (800 mL) for 48 hours. The resulting slurry was filtered under a rubber dam, and the cake was washed with methanol (20 mL). The filtrate was concentrated under vacuum to a yellow solid (56.80 g, 20.9% yield by HPLC; total overall yield 88.7%A). This extract was also taken to the N-BOC derivative (see the following Example).

EXAMPLE 13

(±)-cis-tert-Butyl N-[4(hydroxymethyl)-2-cyclopenten-1-yl] carbamate

The first extract of the previous example containing (+)-cis4-Amino-2-cyclopentene-1-methanol (0.4459 mol) was dissolved in 2:1 1,4dioxane-water (1.2 L). Sodium bicarbonate (48.69 g, 0.580 mol) was added, the mixture was cooled in an ice-water bath and di-tert-butyidicarbonate (110.25 g, 0.490 mol, Aldrich 97%) was added in one portion with rapid stirring. The resulting mixturewas warmed to room temperature overthe course of one hour, then was concentrated under vacuum to a volume of about 400 mL. The slurry was taken up in chloroform (300 mL), the phases were separated, and the aqueous (upper) phase was reextracted with chloroform (five portions of 300 mL each) until no product was observed in the extract by TLC (silica, 10% mmethanol-chloroform, iodine visualization, R$_f$=0.51). The combined organic phases were dried over sodium sulfate, filtered and concentrated under vacuum to give the title compound as an oil. The final extract of the previous exampie was reacted similary, and the crude title compound thus obtained was combined with the above portion, the combined material was taken up in hexanes and evaporated under vacuum to remove residual chloroform. The oil then crystallized spontaneously. It was triturated in cold hexanes and filtered to give the crude title compound as a crystalline solid, which was dried by suction to a constant weight (79.98 g, 0.3750 mol). Recrystallization from boiling ethyl acetate (70 mL) and hexanes (300 mL) gave the title compound as a off-white, crystalline solid (73.43 g, 0.3443 mol), m.p. 54-5.5.5° C.; $^1$H-NMR (DMSO-d$_6$) δ: 6.72 (d, J=7.9 Hz, 1H, NH), 5.80 and 5.60 (two m, 2H, CH=CH), 4.59 (t, J=5.2 Hz, 1H, OH), 4.45 (m, 1H, CHN), 3.35 (m, overlapping H$_2$O, CH$_2$O), 2.60 (m, 1H, CH), 2.30 (m, 1H, ½CH$_2$), 1.40 (s, 9H, C(CH$_3$)$_3$), 1.2 (m, 1H, ½CH$_2$).

Anal. Calcd. for C$_{11}$H$_{19}$NO$_3$: C, 61.94; H ,8.98; N. 6.57. Found: C, 52.00; H, 8.99; N, 6.55.

The mother liquors were combined, chromatographed on silica gel (700 g, 30% ethyl acetate-hexanes and 5% methanol-chloroform), and crystallized as above to give a second portion of the title compound (10.49 g, 0.0492 mmol). The total yield was thus 0.3935 mol, or 88.9% of theoretical from the starting (±)-2-azabicyclo [2.2.1] hept-5-en-3-one (corrected for aliquots taken).

EXAMPLE 14

(+)-cis-4-Amino-2-cyclopentene-1-methanol

By the method of Examples 11 and 12, but on about twice the scale (97.40 g, 0.8924 mol of (±)-2-azabicyclo[2.2.1] hept-5-en-3-one) the title compound was obtained as extracts containing the title compound (0.7926 mol, 88.8% of theoretical, allowing for aliquots removed, as determined bythe method of Example 3).

EXAMPLE 15

(+)-cis-tert-Butyl N-(4-[hydroxymethyl)-2-cyclopenten-1-yl] carbamate

The combined tetrahydrofuran extracts from the preceding Example were concentrated under vacuum to 1031 g, cooled in an ice-water bath, and a mixture of sodium bicarbonate (97.46 g, 1.16 mol) in water (500 mL) was added. This was followed by di-tert-butyl dicarbonate (204.59), 0.9501 mol). The mixture was stirred at 5° C. for two days. The methanol extracts from the preceding Example were evaporated to an oily solid (136.64 g), which was added to the mixture. After warming to room temperature, the organic solvents were evaporated under vacuum, and the resulting slurrywas extracted with hexanes, three portions of methylene chloride, then hexanes again (200 mL each). The organic extracts were evaporated to an oil, which was crystallized from hexanes (about 300 mL), giving the title compound (154.15 g, 0.7229 mol), identical to the product of Example 13. Additional product was obtained by chromatography of the mother liquors (10.5 g, 0.0491 mol, 86.6% of theoretical from the starting lactam, allowing for aliquots removed).

EXAMPLE 16

(±)cis4-Amino-2-cyclopentene-1-carboxylic acid, methanesulfonate

Beginning with (±)-2-azabicyclo[2.2.1] hept-5-en-3-one (5.111 g, 46.83 mmol, Cambridge), by the method of Example 1, was prepared the title compound (10.268 g, 45.99 mmol, 98.2%); m.p. 137-139° C.; 1H-NMR (DMSOd$_6$) δ: 12.6 (br s, 1H, CO$_2$H), 8.04 (br s, 3H, NH$_3^+$), 6.10 (dt, J=5.6, 2.0, 2.0 Hz, 1H, vinyl), 5.85 (dt, J=5.3, 2.3, 2.3 Hz, 1H, vinyl), 4.19 (br s, w½=20 Hz, 1H, allylic H), 3.61 (m, w½=22 Hz, 1H, allylic H). 2.53 (quintet, J=5.3 Hz overlapping with DMSO peak), ½ CH$_2$), 2.39 (s, 3H, CH$_3$SO$_3$H), 1.93 (dt, J=6.7, 13.7 Hz, 1H, ½CH$_2$); Cl-MS (CH$_4$): 128 (M+1); El-MS: 127 (M).

Anal. Calcd for C$_7$H$_{13}$NO$_5$S: C, 37.66; H, 5.87; N, 6.27; S, 14.36 Found: C, 37.60; H, 5.85; N, 6.25; S, 14.30

EXAMPLE 17

(±)-cis-4-Amino-2-cyclopentene-1-carboxylic acid, 4-toluenesulfonate

To a solution containing a catalytic amount of 4-toluene sulfonic acid (10 mg) in 30% aqueous hydrogen peroxide (0.30 mL, 2.7 mmol) was added 3-tosyl-2-azabicyclo [2.2.1] hepta-2,5-diene (369 mg, 1.49 mmol), prepared by the method of J. C. Jagt and A. M. van Leusen, J. Org. Chem. 1974, 39, 564-566, in portions, with rapid stirring. A large exotherm is noted, stabilizing at 75° C. during the last half of the addition. After stirring 70° C. for 40 minutes, the mixture was repeatedly diluted with water (6 mL total) and filtered until a clear solution resulted. The solution was evaporated to an oil which crystallized (349 mg). This was triturated in tetrahydrofuran, filtered, and dried under vacuum to give the title compound (202 mg, 45.2% of theoretical), $^1$H-NMR spectrum identical to the product of Example 11.

EXAMPLE 18

(±)-(1R*, 2S*), 4S*)-4-[2-Amino-6-[Cyclopropylmethylamino)-9H-purin-9-yl]-2-(hydroxymethyl)-1-cyclopentanol Dihydrochloride)

(±)-(1R*, 2S*, 4S*)-4-(2-Amino-6-chloro-9H-purin-9-yl)-2-(hydroxymethyl)-1-cyclopentanol (250 mg, 0.88 mmol) (Shealy et al.; U.S. Pat. No. 4,543,255; Sep. 24, 1985) ethanol (1 mL), and cyclopropylmethylamine (4.0 mL) were refluxed under nitrogen for 1.5 hours. The cooled solution was evaporated to dryness afterthe addition of 1N sodium hydroxide (0.88 mL). The residue was absorbed on silica gel. Title compound was eluted from a silica gel column with 5% methanol-chloroform as a colorless glass (220 mg). The glass was dissolved in absolute ethanol (8.5 mL) and diluted with 1M hydrochloric acid in diethyl ether (5 mL). The resulting white precipitate was washed with diethyl ether and dried to give the dihydrochloride of title compound as white powder (210 mg, 48%), m.p.>250° C.; mass spectrum (Cl), 301 (M+1).

Anal. Calcd. for C$_{15}$H$_{22}$N$_6$O$_2$·2HCl: C, 46.04, H, 6.18, N, 21.48; Cl, 18.12. Found: H, 6.21; N, 21.36; Cl, 18.05.

EXAMPLE 19

(±)-(1R*, 2S*, 4S*)-4-[2-Amino-6-(cyclopropylamino)-9H-purin-9-yl]-2-(hydroxymethyl)-1-cyclopentanol Dihydrochloride In the same manner as example 18, with cyclopropylamine, title compound was obtained as its dihydrochioride from ethanol-ether as a white powder (272 mg, 85% yield from 0.9 mmol of the 6-chloropurine), m.p.>250°; mass spectrum (Cl), 305 (M+1).

Anal. Calcd. for C$_{14}$H$_2$O N$_6$O$_2$·2HCl·0.85 H$_2$O: C, 42.83; H, 6.08; N, 21.41; Cl, 18.06. Found C, 42.84; H, 6.08; N, 21.40; Cl, 18.04.

EXAMPLE 20

(+)(1S, 2R, 4)-4R)-4-(6-Chloro-5-formamido-2-isobutyramido-4-pyrimidinyl)-2-(hydroxymethyl)-1-cyclopentanol (1R, 3S, 4R)-tert-Butyl N-(3-hydroxy-4-(hydroxymethyl)-1-cyclopentyl)carbamate (5.00 g, 21.6 mmol) 1N hydrochlonc acid (44 mL), and dioxane (10 mL) were stirred at ambient temperature for two hours. This solution was evaporated to colorless oil (3.92 g). This oil was refluxed with triethylamine (9.0 mL) and N-(4,6-dichloro-5-formamido-2-pyrimidyl) isobutyramide (EP 434450, Jun. 26, 1991) (5.99 g, 21.6 mmol) in t-butyl alcohol (75 mL ) for 1.0 hour. The cooled solution was treated with 1N sodium hydroxide (44 mL) and evaporated to a syrup which was chromatographed on silica cel. The title compound was eluted with MeOH:CHCl$_3$/1:4 as a tan solid foam (6.79 g, 83%). Such a sample was slurried in diethyl ether to give off-white powder, m.p.: collapses at 105-108° C.; mass spectrum (Cl, CH$_4$) 372 (M+1); $^1$H-HMR (DMSO); δ1.06 (d, J=6.8 Hz, 6H), 1.22 (m, 1H), 1.80 (m, 3H), 2.19 (m, 1H), 2.90 (m, 1H), 3.35 (m, 2H), 3.92 (m, 1H), 4.57 (m, 3H), [7.11 (d, J=7.8 Hz), 7.39 (d, J=7.8 Hz), 1H]; [7.89 (d, J=11.4 Hz), 8.16(s), 1H], [8.82 (d, J=11.4 Hz), 9.29(s), 1H], [10.17(s), 10.23(s), 1H]; $[α]^{20}_{589}$+23.6°, $[α]^{20}_{578}$+24.9°, $[α]^{20}_{546}$+28.9°, $[α]^{20}_{436}$+53.4°, $[α]^{20}_{365}$+96.2° (c=0.71, methanol).

Anal. Calcd. for C$_{15}$H$_{22}$N$_5$O$_4$Cl0.45 H$_2$O·0.35 EtOH; C, 45.61; H, 6.36; N, 17.68; Cl, 8.95. Found: C, 47.84; H. 6.19; N, 17.42; Cl, 9.02.

EXAMPLE 21

(±)-(1S, 2R, 4R)-4-(2-Amino-6-chloro-9H-purin-9-yl)-2-(hydroxymethyl)cyclopentanol (1S, 2R, -4R)-4-(6-Chloro-5-formamido-2-isobutyramide-4-pyrimidinyl)-2-(hydroxymethyl)-1-cyclopentanol (6.25 g, 16.8 mmol) was maintained at 55° C. in 1N hydrochloric acid (85 mL) for 4 hours. Evaporation gave a dark oil which was dissolved in N,N-dimethylformamide (20 mL) and triethylorthoformate (85 mL). The resulting solution was stirred at ambient temperature for 16 hours. Volatiles were removed under vacuum and the residual oil stirred in 1N hydrochloricacid (100 mL) for 5 hours. The solution was neutralized with sodium hydroxide and evaporated to a brown syrup. Chromatography on silica gel with methanol:chloroforml 15:85 gave title compound as a solid foam (3.9 g). Crystallization from acetonitriie-methanol (1:1) gave title compound as white crystals (2.59 g, 53%); m.p. 143-144°; mass spectrum (Cl, CH$_4$) 284 (M+1); $^1$H-NMR (DMSO); δ 1.67 (m, 1H), 2.01 (m, 2H), 2.17 (m, 1H), 2.33 (m, 1H), 3.45 (m, 1H), 4.09 (m, 1H), 4.65 (t, J=5.1 Hz, 1H, 4.80 (d, J=4.0 Hz, 1H), 4.91 (m, 1H), 6.88 (br s, 2H), 8.25 (s, 1H), $[\alpha]^{20}_{589}$+17.5°, $[\alpha]^{20}_{578}$+18.3°, $[\alpha]^{20}_{546}$30 20.5°, $[\alpha]^{20}_{436}$+34.2°, $[\alpha]^{20}_{365}$+49.4° (c=0.67, methanol).

Anal. Cald. for $C_{11}H_{14}N_5O_2Cl\cdot0.5\ H_2O$: C, 45.13; H, 5.16; N, 23.92; Cl, 12.11. Found: C, 45.05; H, 5.02; N, 23.73; Cl, 12.13.

EXAMPLE 22

(±) (1S, 2R, 4R)-4-[2-Amino-6-(cyclopropylmethylamino)-9H-purin-9-yl]-2-(hydroxymethyl)-1-cyclopentanol In the same manner as for the racemate, Example 18, title compound was isolated, after chromatography, as white solid foam (48% from 2.0 mmoles of (±)-(1S, 2R, 4R)-4-(2-amino-6-chloro-9H-purin-9yl)-2-(hydroxymethyl) cyclopentanol); m.p. collapses at 79-83°; mass spectrum (Cl, $CH_4$): 319 (M+1); $^1$H-NMR (DMSO-$d_6$) δ: 7.83 (s, 1, H-8), 5.79 (br s, 2, $NH_2$), 4.95–4.80 (m, 1, CHN), 4.75 (d, J=4.0 Hz, 1, OH), 4.64 (t, J=5.2 Hz, 1, $CH_2OH$), 4.05 (br m, 1, CHO), 3.60–3.35 (m, 2, $CH_2O$), 3.25–3.15 (m, overlapping s at 3.25, 4, CHNME, $CH_3$), 2.35–2.20) (m, 1, CH), 2.20–2.0, (m, 1 ½$CH_2$), 2.0–1.85 (m, 2, methylene, 0.85–0.60 (m, 4, 2$CH_2$ of cyclopropyl); $[\alpha]^{20}_{589}$+10.6°, $[\alpha]_{578}$+10.8°, $[\alpha]^{20}_{546+12.3}$°, $[\alpha]^{20}_{436}$+20.6°, $[\alpha]^{20}_{365}$31.3° (c=0.84, methanol).

Anal. Calcd. for $C_{15}H_{22}N_6O_2\cdot0.5\ H_2O\cdot0.04\ EtOH$; C, 55.02; H, 7.11; N, 25.53. Found: C, 55.02; H, 7.06: N, 25.59.

EXAMPLE 23

(±)-(1S, 2R, 4R)-4-[2-Amino-6-(cyclopropylamino)-9H-purin-9-yl]-2-(hydroxymethyl)-1-cyclopentanol (±)-(1S, 2R, 4R)-4-(2-Amino-6-chloro-9H-purin-9-yl)-2-hydroxymethyl) cyclopentanol (425 mg, 1.5 mmol), cyclopropylamine (Aldrich, 1.4 mL), and ethanol (4 mL) were refluxed for 3 hours. To the cooled solution was added 1N sodium hydroxide (1.5 mL). The residual oil left on evaporation of volatiles under vacuum was chromatographed on silica gel. Title compound was eluted with methanol: ethyl acetate/15:85 as a white solid foam which solidified to white powder in methanol-acetonitrile (309 mg, 68%); m.p. 174–176° C.; mass spectrum (Cl, $CH_4$) 305 (M+1); $^1$H-NMR (DMSO-$d_6$) δ: 7.79 (s, 1, H-8); 7.25 (d, J=2.9 Hz, 1, NH), 5.79 (s, 2, $NH_2$), 4.90–4.75 (m, 1, CH—N), 4.73 (d, J=4.0 Hz, 1, OH), 4.63 (t, J=5.3 Hz, 1, CHOH), 4.08–4.00 (m, 1, CHO), 3.58–3.38 (m, 2, $CH_2O$), 3.05–2.95 (m, 1 CH—NH), 2.35–2.20 (m, 1, CH), 2.18–2.0 (m, 1, ½$CH_2$), 2.0–1.9 (m, 2, methylene), 1.7–1.5 (m, 1, ½$CH_2$), 0.70–0.50 (m, 4, 2$CH_2$) of cyclopropyl); $[\alpha]^{20}_{589}$30 7.72°, $[\alpha]^{20}_{578}$+7.87°, $[\alpha]^{20}_{546}$+8.77°, $[\alpha]^{20}_{436}$+14.4°, $[\alpha]^{20}_{365}$+20.1° (c=0.66, methanol).

Anal. Calcd. for $C_{14}H_{20}H_{20}N_6O_2$; C, 55.25; H, 6.62; N, 27.62. Found: C. 55.21; H, 6.59; N. 27.54.

EXAMPLE 24

(±)-(1S, 2R, 4R)-4-(2)-Amino-1,6-dihydro-6-thioxo-9H-purin-9-yl)-2-(hydroxymethyl)-1-cyclopentanol (±)-(1S, 2R, 4R)-4-(2)-Amino-6-chloro-9H-purin-9-yl)-2-(hydroxymethyl)cyclopentanol. (1.70 g, 6.00 mmol) and thiourea (456 mg, 6.00 mmol) were refluxed in water (15 mL) for 1.0 hour. The cooled solution was adjusted to pH5 with saturated aqueous sodium bicarbonate. The resulting precipitate was filtered, washed with water and dried to give title compound as white powder (1.20 g, 71%); m.p. 290-291° dec; mass spectrum (Cl, $CH_4$) 282 (M+1); $^1$H-NMR (DMSO-$d_6$) δ: 11.90 (br s, 1, NH), 8.03 (s, 1, H-8), 6.78 (br s, 2, $NH_2$), 4.95–4.70 (m, overlapping d at 4.78, J=2.7 Hz, total 2, CHN and OH). 4.7–4.6 (m, 1, $CH_2OH$), 4.1–4.0 (m, 1, CHOH), 3.6–3.4 (m, 2, $CH_2O$), 2.4–2.2 (m, 1, CH), 2.2–1.9 (m, 3, methylene, 1.7–1.5 (m, 1 ½$CH_2$; $[\alpha]^{20}_{568}$+6.43°, $[\alpha]^{20}_{578}$+6.71°, $[\alpha]^{20}_{546}$+7.43°, $[\alpha]^{20}_{436}$+8.43°, $[\alpha]^{20}_{365}$+8.43° (c=0.70, 0.1N, NaOH).

Anal Calcd. for $C_{11}H_{15}N_5SO_2$: C, 49.96; H, 5.37; N, 24.90; S, 11.40 Found: C, 46.83; H, 5.40; N, 24.88; S, 11.47.

EXAMPLE 25

(±)-(1S, 2R, 4R)-4-[2-Amino-6-(1-pyrrolidinyl)-9H-purin-9-yl]-2-(hydroxymethyl-1-cyclopentanol (±)-1S, 2R, 4R)-4-(2-Amino-6-chloro-9H-purin-9-yl)-2-hydroxymethyl)cyclopentanol (426 mg 1.5 mmol), pyrrolidine (99%, Aldrich, 1.26 mL), and ethanol (8 mL) were refluxed for 20 minutes. To the coded solution was added 1N sodium hydroxide (1.5 mL). Volatiles were evaporated and the residue chromatographed on silica gel. Title compound was eluted with 12% methanol-chloroform as a white solid foam which solidified from 95% ethanol to white powder (324 mg, 64%); mp 114-170°; mass spectrum (Cl, $CH_4$): 319 (M+1); $^1$H-NMR (DMSO-$d_6$) δ: 7.81 (s, 1, H-8), 5.76 (br s, 2, $NH_2$), 5.0–4.8 (m, 1, CHN), 4.76 (d, j=4.1 Hz, 1, OH), 4.66 (t, J=5.2 Hz, 1, $CH_2OH$), 4.15–4.0 (m, overlapping br m at 4.1–3.4 and m at 3.6–3.35, total 7, CHO, 2$CH_2N$ and $CH_2O$), 2.4–2.2 (m, 1, ½$CH_2$), 2.2–1.8 (m, 7, methylenes), 1.7–1.5 (m, 1, ½$CH_2$); $[\alpha]^{20}_{589}$+10.5°, $[\alpha]^{20}_{578}$+11.0°, $[\alpha]^{20}_{546}$+12.4°, $[\alpha]^{20}_{436}$+19.5°, $[\alpha]^{20}_{365}$+25.5° (c=1.43, methanol.

Anal. Calcd. for $C_{15}H_{22}N_6O_2\cdot0.2H_2O\cdot0.03\ EtOH$: C. 55.80; H, 7.26; N, 25.03. Found, C. 56.01; H, 7.31; N, 24.82.

EXAMPLE 26

(±)-(1S, 2R, 4R)-4-[6-(allylthio)-2-amino-9H-purin-9yl)-2-(hydroxymethyl-1-cyclopentanol (+)-(1S, 2R, 4R)-4-(2-Amino-1,6-dihydro-6-thioxo-9H-purin-9-yl)-2-hydroxymethyl)-1-cyclopentanol (351 mg, 1.25 mmol) and 1N sodium hydroxide (1.25 mL) were stirred with allyl chloride (0.15 mL) for 5 hours. The solution was neutralized with hydrochloric acid and volatiies evaporated. The residue was chromatographed on silica get. Title compound was eluted with 12% methanol-chloroform as a white solid foam which solidified to white powder from acetonitrile (240 mg, 60%); m.p. 133-134°; mass spectrum (Cl, $CH_4$):322 (M+1); $^1$H-NMR (DMSO $d_6$) δ: 8.07 (s, 1, H8), 6.51 (br s, 2, $NH_2$), 6.10–5.85 (m, 1CH=), 5.45–5.30 (m, 1, ½$CH_2$=), 5.15–5.05 (m, 1, ½$CH_2$=), 5.0–4.8 (m, 1, CHN), 4.79 (d, J=4.1 Hz, 1, OH), 4.66 (t, J=5.2 Hz, 1, $CH_2OH$), 4.15–4.0 (m, 1, CHO), 3.98 (d, J=6.9 Hz, 2, $CH_2S$), 3.6–3.4 (m, 2, $CH_2O$), 2.14–1.9 (m, 4, CH+methylenes), 1.75–1.55 (m, 1, ½$CH_2$); $[\alpha]^{20}_{589}$+9.30°, $[\alpha]^{20}_{578}$+9.58°, $[\alpha]^{20}_{546}$+11.1°, $[\alpha]^{20}_{436}$+18.6°, $[\alpha]^{20}_{365}$30 25.4° (c=0.79, methanol).

Anal. Calcd. for $C_{14}H_{19}N_5O_2S$; C, 52.32; H, 5.96; N, 21.79; S, 9.98. Found: C, 25.35; H, 5.94; N, 21.82; S, 9.88.

EXAMPLE 27

(±) (1S, 2R, 4)-4[2-amino-6-(1-azetidinyl)-9H-purin-9-yl]-2-(hydroxymethyl)-1-cyclopentanol (±)-(1 S, 2R, 4R)-4-(2-Amino-6-chloro-9H-purin-9-yl)-2-hydroxymethyl)cyclopentanol (340 mg, 1.20 mmol) and azetidine (98%, ALdrich, 1.0 mL) and methanol (6 mL) were maintained at 60° C. in a sealed tube for 18 hours. To the cooled solution was added 1N sodium hydroxide (1.2 mL). Volatiles were evaporated and the residue chromatographed on silica gel. Title compound was eluted with methanol: ethyl acetate/15:85 as a white foam which solidified to white powder from methanol-acetonitrile (333 mg, 91%), mp 194-195; mass spectrum (Cl, $CH_4$) 305 (M+1); $^1$H-NMR ($DMSO_6$) δ: 7.81 (s, 1, H8), 5.88 (br s, 2, $NH_2$), 4.95–4.80 (m, 1, CH—N), 4.76 (d, J=3.9 Hz, 1, OH), 4.66 (t, J=5.0 Hz, 1, $CH_2$—OH). 4.4–4.15 (br m, 4, $2CH_2N$), 4.10–4.0 (m, 1, CHO), 3.6–3.4 (m, 2, $CH_2O$), 2.5–1.9 (m, 6, methylene), 1.75–1.5 (m, 1, $½CH_2$); $[α]^{20}_{589}+10.1°$, $[α]^{20}_{578}+10.7°$, $[α]^{20}_{540}+11.9°$, $[α]^{20}_{436}+18.3°$, $[α]^{20}_{365}+25.2°$ (c=0.812, methanol).

Anal. Calcd. for $C_{14}H_{20}N_6O_2$: C, 55.25; H, 6.62; N, 27.62. Found: C, 55.3 1; H, 6.63; N, 27.71.

EXAMPLE 28

(±)-(1S, 2R, 4R)-4-(2-Amino-6-(cyclopentyloxy)-9H-purin-9-yl)-2-(hydroxymethyl)-1-cyclopentanol Sodium hydride (60% oil dispersion, 113 mg) was added to cyclopentanol (7 mL). To the resulting solution, after effervescence had ceased, was added (±)-(1S-2R-4R)-4-(2-amino-6-chloro-9H-purin-9-yl)-2-hydroxymethyl) cyclopentanol (400 mg, 1.4 mmol). The solution was maintained at 85° for 40 minutes, cooled to room temperature, and neutralized with 1N hydrochloric acid. Volatiles were removed and the residue chromatographed on silica gel. Title compound was eluted with methanol: chloroform/15:85 as a white solid foam which solidified form acetonitrile: methanol/20:1 as a white powder (223 mg, 48%), m.p. 181-182°; mass spectrum (Cl, $CH_4$): 334 (M+1); $^1$H-NMR (DMSO-$d_6$) δ: 7.97 (s, 1, H8), 6.32 (br s, 2, $NH_2$), 5.60 (m, 1, CHO of cyclopentyl) 5.0–4.8 (m, 1, CHN), 4.78 (d, J=4.1 Hz, 1, OH), 4.66 (t, J=5.1 Hz, 1, $CH_2OH$), 4.1 (m, 1, CHOH), 3.6–3.4 (m, 2, $CH_2O$), 2.4–1.9 (m, 6 methylene), 1.9–1.5 (m, 7, methylene); $[α]^{20}_{589}+9.34°$, $[α]^{20}_{578}+9.85°$, $[α]^{20}_{546}+11.1°$, $[α]^{20}_{430}+18.2°$, $[α]^{20}_{365}+26.6°$ (c=0.782, methanol).

Anal. Calcd. for $C_{16}H_{23}N_5O_3$: C, 57.65; H, 6.95; N, 21.01. Found: C, 57.74; H, 6.94; N, 20.91.

EXAMPLE 29

(1S, 4R)-[2-(2-Amino-6-chloro-4-pyrimidinyl) amino]-2-cyclopentene-1-methanol

A solution of (−)-2-azabicyclo[2.2.1hept-5-en-3-one (Enzymatix lot #LN 1253, 30.0 g, 275 mmol) in anhydrous tetrahydrofuran (150 mL) in a 2 L 3-neck round bottom flask under nitrogen was equipped with a thermometer and mechanical stirrer, then warmed to 35° C. (most of solid dissolved). Meanwhile, a solution of methanesulfonic acid (28.0 g, 291 mmol) and water (5.35 g, 297 mmol) in tetrahydrofuran (50 mL) was prepared (caution-mixing is highly exothermic). This solution was slowly added dropwise via an addition funnel to the 2 L flask over 10 min. Initially the solution became turbid, and bythe end of the addition some solid had appeared on the side of the flask. The mixture was heated to gentle reflux for 3 h (internal temperature 62-65° C.), then cooled (−15° C.). An air-dried sample of the white solid had 1H-NMR identical with the sample of (−)-(1S, 4R)-4-amino-2-cyclopentene-1-carboxylic acid methanesulfonate described in Example 1. A solution of 1.0 N lithium aluminurm hydride in tetrahydrofuran (Aldrich, 525 mL, 525 mmol) was added dropwise to the mixture (slowly at first, more rapidly later) so that pot temperature remained below 0° C. After addition was complete (required approx. 35 min) the mixture was slowly warmed to 22° C. and stirred at room temperature for 17 h, then refluxed for 5 h and cooled to ambient. Sodium fluoride (150 g, 3.57 mol) was added, stirring was continued for 30 min, then the mixture was cooled on an ice bath (5° C.). Water (38 g, 2.1 mol) was added dropwise so that pot temperature remained below 20° C. (over 30 min), then the mixture was stirred at room temperature for 20 m inand filtered. The filter cake was washed with tetrahydrofuranimethanol (5:2), and the filtrate was set aside. The filter cake was taken up in tetrahydrofuranimethanol (5:2, 700 mL), stirred for 15 min, and filtered. This extraction was repeated and the three filtrates were combined and cooled (0° C.), then refiltered. A 1 mL aliquot of this solution was concentrated to give (−)-(1S, 4R)-4-amino-2-cyclopentene-1-methanol as a colorless oil with identical analysis to the sample described in Example 2 and 3. The remainder of the solution was partially concentrated in vacuo, diluted with 1-butanol (500 mL), further concentrated to remove tetrahydrofuran and methanol, and transferred to a 1 L 3-neck flask under nitrogen equipped with a thermometer and reflux condenser. Triethylamine (125 mL. 900 mmol) and 2-amino-4,6-dichloropynmidine (47.0 g, 286 mmol) were added, and the mixture was refluxed for 4 h (internal temperature 107-108° C.). The reaction solution was partially concentrated in vacuo and treated with 5N sodium hydroxide (60 mL, 300 mmol). The solution was concentrated in vacua, diluted with toluene (100 mL), and further concentrated in order to remove the remaining triethylamine. The residual oil was taken up in chloroform (500 mL) and methanol (100 mL), then the mixture was filtered. The filter cake was washed with methanol/chloro-form (1:9), then the filtrate was concentrated in vacuo and the residual oil dissoived in chloroform and loaded onto a column of silica gel containing 300 g of silica. The column was initially eluted with 3% ethanol/chloroform, then with 8% ethanol/chloroform to afford pure fractions of the subject compound; these were concentrated in vacuo to constant weight to afford (1S, 4R)-[2-(2-amino-6-chloro-4-pyrimidinyl)amino]-2cyclopentene-1-methanol as a pale tan gum (53.1 g, 75%); mp 73-75° C. as a pale tan solid hydrate (methanollwater). 1H-NMR (DMSO-$d_6$): 7.00–7.10 (br s, 1H); 6.35-6.45(br s, 2H); 5.87 (m, 1H); 5.73 (s, 1H); 5.71 (m, 1H); 4.90-4.05 (br s, 1H); 4.64 (t, 1H, J=5Hz); 3.36 (m, 2H); 2.6-2.75 (m, 1H); 2.30-2.40 (m, 1H); 1.20-1.30 (m, 1H). Ms (Cl): m/z 241 (m+H+, 100). $[α]^{20}_{589}−27.3°$ (c=0.54, methanol.

Anal. Calcd for $C_{10}H_{13}ClN_4O·H_2O$: C, 46.43; H, 5.84; N, 21.66. Found: C, 46.49; H, 5.81; N. 21.79.

EXAMPLE 30

(1S, 4R)-4-((2-Amino-6-chloro-5-((4-chlorophenyl) azo)-4-pyrimidinyl)amino)-2-cyclopentene-1-methanol An ice cooled (5° C.) solution of 4-chloroaniline (5.74 g, 45 mmol) in a mixture of water (50 mL) and concentrated hydrochloric acid (13.6 mL) was treated dropwise with a cooled (5° C.) solution of sodium nitrite (3.11 tg, 45 mmol) in water (25mL) at a rate to keep the pot temperature below l0lC This solution was placed in a dropping funnel and added dropwise to a mechanically stirred, cooled (5° C.) solution of sodium acetate trihydrate (49 g, 360 mmol) and (1S, 4R)-(2-(2-amino-6-chloro-4-pyrimidinyl)amino)-2- cyclopentene-1-methanol hydrate (9.99 g, 40 mmol) in water/acetic acid (1:1, 100 mL) at a rate to keep the pottemperature below 10° C. The mixture was warmed and stirred at room temperature for 18 h, then filtered. The filter cake was washed with water, air dried, and triturated from acetonitrile to afford 14.26 g (91%) of the title compound as a hydrate (1:0.75); mp 218-20° C. (dec). $^1$H NMR (DMSO-$d_6$): 10.25 (d, 1H, J=7 Hz); 7.70 (d, 2H, J=9 Hz); 7.55 (d, 2H, J=9 Hz); 5.94 (m, 1H); 5.83 (m, 1H); 5.20-5.30 (m, 1H); 3.35-3.50 (m, 2H); 2.70-2.80 (m, 1H); 2.40-2.50 (m, 1H); 1.40-1.55 (m, 1H), Ms (Cl): m/z 283 (m-C5 ring, 60); 343 (m-Cl, 40); 379 (m+H$^+$, 100). $[\alpha]^{20}_{589}$+26.8° (c=0.51, methanol).

Anal. Calcd for $C_{16}H_{16}Cl_2N_6O \cdot 0.75H_2O$: C, 48.93; H, 4.49; N, 21.40. Found: C, 49.02; H, 4.51; N, 21.42.

EXAMPLE 31

(1S, 4R)-(4-(2,5-Diamino-6-chloro-4-pyrimidinyl) amino)-2-cyclopenten-1-methanol A suspension of (1S, 4R)-4-((2-amino-6-chloro-5-((4-chlorophenyl)azo)-4-pyrimidinyl)-amino)-2-cyclopentene-1-methanol hydrate (0.76 g, 2.0 mmol) in methanol/acetic acid/water (6:2:1, 9 mL) was treated in portions over 10 min with zinc powder (1.0 g, 15.3 mmol) so that the pot temperature remained below 35° C. The mixture was stirred at room temperature for 1 h and at 40° for 1 h, then concentrated in vacuo with addition of toluene to remove acetic acid and water. The residue was taken up in 5% isopropanol-chloroform and loaded onto a silica gel column, which was eluted with 8% isopropanol-chloroform, then with 15% isopropanol-chloroform to afford pure fractions of the subject compound, which were combined and concentrated in vacua to afford (1S, 4R)-(4-(2,5-diamino-6-chloro-4-pyrimidinyl)amino)-2-cyclopenten-1-methanol as a pink-tan solid (0.39 g, 76%); mp 159.5-161.0° C. $^1$H NMR (DMSO-$d_6$): 6.41 (d, 1H, J=7 Hz); 5.85-5.95 (m, 1H); 5.70-5.80 (m, 1H); 5.62 (br s, 2H); 5.00-5.15 (m, 1H); 4.67 (t, 1H, J=5 Hz); 3.96 (br s, 2H); 3.35-3.45 m, 2H); 2.60-2.80 (m, 1H); 2.30-2.50 (m, 1H); 1.20-1.40 (m, 1H). Ms (Cl): m/z 160 (m-C5 ring, 90); 220 (m-Cl, 40); 255 (m+H$^+$, 100). $[\alpha]^{20}_{589}$+0.37°, $[\alpha]^{20}_{436}$−9.41° (c=0.54, methanol).

Anal. Calcd for $C_{10}H_{14}ClN_5O$: C, 46.97; H, 5.52; N, 27.39. Found: C, 47.03; H, 5.54; N, 27.45.

EXAMPLE 32

(1S, 4R)-4-(2-Amino-6-chloro-9H-purin-9-yl)-2-cyclopentene-1-methanol

A suspension of (1S, 4R)-4-((2-Amino-6-chloro-5-((4chlorophenyl)azo)4-pyrimidinyl)amino)-2-cyclopentene-1-methanol hydrate (1.96 g, 5 mmol) in tetrahydrofuran (15 mL) was treated with acetic acid/water (1:1, 5 mL), then with zinc dust (1.63 g, 25 mmol) in portions so as to keep the pot temperature below 35° C. The deep yellow color faded after 10 min. and after an additional 50 min the solution was filtered to remove precipitated zinc salts. The filter cake was rinsed with tetrahydrofuran and the filtrate was refiltered to remove additional zinc salts, then concentrated in vacuo with addition of toluene to facilitate removal of water and acetic acid. The residue was rinsed with toluene/hexane to separate some of the 4-chloroaniline byproduct, taken up in triethyl orthoformate (40 mL), cooled on an ice bath (5° C.), and treated dropwise with concentrated hydrochloric acid (1.9 mL). The mixture was stirred at 5° C. for 5 h (tan suspension soon formed), slowdy warmed to room temperature, and stirred for an additional 18 h, then cooled on an ice bath and filtered. The filter cake was rinsed with ether (save filtrate), and this solid was taken up in water (30 mL), filtered, and the solids washed with water. The aqueous filtrate was basified with sodium carbonate to pH-9, then extracted with 5% isopropanol-chloroform (3×25 mL). The combined extracts were dried ($Na_2SO_4$) and concentrated in vacuo to a residual tan foam (0.85 g). The organic filtrate from above wasconcentrated in vacuoand the residue taken up in 1 N hydrochloric acid (30 mL), stirred for 1 h, filtered, and the filtrate adjusted to pH-6 with 5 N sodium hydroxide (6 mL), then basified with sodium carbonate. This aqueous suspension was extracted with 5% isopropanol-chloroform (3×25 mL), and the combined organic extracts were dried ($Na_2SO_4$) and concentrated in vacua to a tan foam (0.55 g). The two batches were combined, dissolved in warm chloroform, and loaded onto a silica gel column, which was eluted with 7% methanol-chloroform to afford pure fractions containing the subject compounds. These were concentrated in vacua and the residual foam crystallized from ethyl acetate (2 crops) to afford 0.869 (65%) of the title compound as a pale tan solid; mp 160-162° C. $^1$H-NMR(DMSO-$d_6$) δ: 8.04 (s, 1H); 6.91 (s, 2H); 6.15 (m, 1H); 5.90 (m, 1H); 5.45 (m, 1H); 4.73 (t, 1H, J=5 Hz); 3.45 (t, 2H, J=5 Hz; 2.80-2.95 (m, 1H); 2.55-2.70 (m, 1H); 1.60-1.70 (m, 1H ). Ms (Cl): m/z 170 (m-C5 ring, 100); 230 (m-Cl, 50); 266 (m+H$^{+,}$ 100). $[\alpha]^{20}_{589}$−104°, $[\alpha]^{20}_{436}$−267° (c=0.29, methanol).

Anal. Calcd for $C_{11}H_{12}ClN_5O$: C, 49.73; H, 4.55; N, 26.36. Found: C, 49.89; H, 4.61; N, 26.25.

EXAMPLE 33

(−)-1S, 4R)-4-[2-Amino-6-(cyclopropylmethylamino)-9H-purin-9-yl]-2-cyclopentene-1-methanol (1S, 4R)-4-(2-amino-6-chloro-9H-purin-9-yl)-2-cydcopentene-1-methanol (274 mg, 1.00 mmol), N-cyclopropyl-N-methylamine (0.71 g, 10 mmol) and absolute ethanol were refluxed for 5.0 hpurs. Volatiles were evaporated and the residue chromatograped on silica gel. Title compound was eluted with 10% methanol-chloroform as a colorless glass. Evaporation of an ethanol solution gave title compound as a colorless solid foam (293 mg, 98%). $^1$H-NMR (DMSO-$d_6$) δ: 0.56 and 0.63 (2m, 4,2-cyclopropyl $CH_2$), 1.56 and 2.60 (2m, 2, cyclopentenyl $CH_2$), 2.85 (m, 1, H-4'), 3.02 (m, 1, cyclopropyl CHNH); 3.43 (m, 2, $CH_2OH$), 4.71 (t, 1, $CH_2OH$); 5.40 (m, 1, H-1'), 5.85-5.70 (m overlapping s at 5.77, 3, $NH_2$ and =CH), 6.09 (m, 1, =CH), 7.23 (d, 1, NHCH), 7.58 (s, 1, purine H-8); ms (Cl) 287 (m+1). $[\alpha]^{20}_{589}$+59.7°, $[\alpha]^{20}_{436}$+128° (c=0.15, methanol).

Anal. Calcd. for $C_{14}H_{18}N_6O \cdot 0.15$ EtOH·0.05 $H_2O$: C, 58.39; H, 6.51; N, 28.57, Found: C, 58.11; H, 6.84; N, 28.92.

EXAMPLE 38

(+)-(1R, 4S)-4-Amino-2-cyclopentene-1-methanol

A mixture of (−)-(1S, 4R)-4-amino-2-cyclopentene-1-carboxylic acid (chiros Ltd., Cambridge, England; 40.00 g, 0.315 mole) in dry tetrahydrofuran (300 mL) was stirred in an ice bath while 1 M lithium aluminum hydride in tetrahydrofuran (Aldrich, 485 mL) was added over 1.5 hours. The temperature during this addition was not allowed to exceed 0° C. The mixture was broughtto ambient temperature and then to reflux over one hour and maintained at reflux for 2.5 hours. The mixture was allowed to cool to ambient temperature and sodium fluoride (89.6 g) was added and stirring continued for an additional 0.5 hour. The mixture was cooled (ice bath) and water (23 mL) added slowly. Stirring was continued for an additional 0.5 hour. The precipitate was filtered and extracted with 40% methanol-tetrahydrofuran (2×300 mL). The filtrate-wash was concentrated in vacuo to a colorless oil which darkened rapidly in air and light. Such a sample was dried at ambient temperature/0.2 mm Hg to a pale yellow oil; $^1$H-NMR (DMSO-$d_6$) identical to that of the enantiomer described in Example 1, d: 5.67 (m, 2, CH=CH), 3.8–3.7 (m, 1, CHN), 3.32 (d, J=6.0 Hz, over-lapped by broad D$_2$O-exchangeable peak centered at 3.18, CH$_2$O, OH, NH$_2$ and H$_2$O in solvent), 2.68–2.56 (m, 1, H-1), 2.28–2.18 (m, 1, ½CH$_2$), 1.08–0.98 (m, 1, ½ CH$_2$); mass spectrum (Cl): 114 (M+1); $[\alpha]^{589}+55.0°$, $[\alpha]^{20}_{578}+58.3°$, $[\alpha]^{20}_{546}+67.4°$, $[\alpha]^{20}_{436}+119°$ (c=0.242, methanol).

Anal. Calcd. for C$_6$H$_{11}$NO·0.31 H$_2$O: C, 60.69; H, 9.86; N, 11.80. Found: 61.12; H, 9.79; N, 11.38.

What is claimed is:

1. (±)-cis-tert-Butyl N-[4-(hydroxymethyl)-2-cylcopenten-1-yl] carbamate.
2. (−)-(1R, 4S)-tert-Butyl N[4-(hydroxymethyl)-2-cyclopenten-1-yl] carbamate.
3. (±)-(1S, 4R)-tert-Butyl N-[4-(hydroxymethyl)-2-cylcopenten-1-yl] carbamate.

* * * * *

UNITED STATES PATENT AND TRADEMARK OFFICE
CERTIFICATE OF CORRECTION

PATENT NO. : 6,392,085 B2
DATED : May 21, 2002
INVENTOR(S) : Daluge et al.

It is certified that error appears in the above-identified patent and that said Letters Patent is hereby corrected as shown below:

Column 36,
Line 7, delete "cylcopenten" and insert therefore -- cyclopenten --.
Line 8, delete "N[4" and insert therefor -- N-[4 --.
Line 10, delete "±" and insert therefor -- + --.
Line 11, delete "cylcopenten" and insert therefore -- cyclopeneen --.

Signed and Sealed this

Twenty-fifth Day of January, 2005

JON W. DUDAS
*Director of the United States Patent and Trademark Office*